US008618161B2

(12) United States Patent
Lam et al.

(10) Patent No.: US 8,618,161 B2
(45) Date of Patent: *Dec. 31, 2013

(54) FLUORESCENT POLYMERIC MATERIALS CONTAINING LIPID SOLUBLE RHODAMINE DYES

(75) Inventors: Joe Y. L. Lam, Castro Valley, CA (US); Steven M. Menchen, Fremont, CA (US); Ruiming Zou, Foster City, CA (US); Scott C. Benson, Alameda, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/026,690

(22) Filed: Feb. 14, 2011

(65) Prior Publication Data
US 2011/0226994 A1 Sep. 22, 2011

Related U.S. Application Data

(60) Continuation of application No. 12/240,194, filed on Sep. 29, 2008, now abandoned, which is a division of application No. 10/837,983, filed on May 4, 2004, now Pat. No. 7,432,298.

(60) Provisional application No. 60/469,030, filed on May 9, 2003.

(51) Int. Cl.
*A61K 31/352* (2006.01)
*C07D 311/92* (2006.01)

(52) U.S. Cl.
USPC .......................................... 514/453; 549/382

(58) Field of Classification Search
USPC .................... 514/453; 549/224, 382
See application file for complete search history.

(56) References Cited

U.S. PATENT DOCUMENTS

| 738,227 A | 9/1903 | Nastvogel |
|---|---|---|
| 1,532,790 A | 4/1925 | Weiler |
| 2,447,440 A | 8/1948 | Thurston et al. |
| 2,535,968 A | 12/1950 | Thurston et al. |
| 3,079,435 A | 2/1963 | Freifelder et al. |
| 4,318,846 A | 3/1982 | Khanna et al. |
| 4,329,461 A | 5/1982 | Khanna et al. |
| 4,439,356 A | 3/1984 | Khanna et al. |
| 4,445,904 A | 5/1984 | Hähnke et al. |
| 4,481,136 A | 11/1984 | Khanna et al. |
| 4,581,071 A | 4/1986 | Akutsu et al. |
| 4,640,893 A | 2/1987 | Mangel et al. |
| 4,983,498 A | 1/1991 | Rode et al. |
| 5,066,580 A | 11/1991 | Lee |
| 5,188,934 A | 2/1993 | Menchen et al. |
| 5,231,191 A | 7/1993 | Woo et al. |
| 5,366,860 A | 11/1994 | Bergot et al. |
| 5,389,489 A | 2/1995 | Yanagihara et al. |
| 5,410,053 A | 4/1995 | Hahn et al. |
| 5,442,045 A | 8/1995 | Haugland et al. |
| 5,654,419 A | 8/1997 | Mathies et al. |
| 5,654,442 A | 8/1997 | Menchen et al. |
| 5,750,409 A | 5/1998 | Hermann et al. |
| 5,800,996 A | 9/1998 | Lee et al. |
| 5,840,999 A | 11/1998 | Benson et al. |

(Continued)

FOREIGN PATENT DOCUMENTS

| AU | 5227898 | 6/1998 |
|---|---|---|
| CA | 2119840 A1 | 9/1994 |

(Continued)

OTHER PUBLICATIONS

European Application No. 04 760 869.0, EPC Office Communication mailed Oct. 6, 2010.
PCT/US2004/013798; International Preliminary Report on Patentability mailed Nov. 24, 2005; 5 pages.
Panchuk-Voloshina et al., 1999, "Alexa Dyes, a Series of New Fluorescent Dyes that Yield Exceptionally Bright, Photostable Conjugates, J. Histochemistry & Cytochemistry," 47(9):1179-1188.
Tsukanova et al., 2002, "Microscopic Organization of Long-Chain Rhodamine Molecules in Monolayers at the Air/Water Interface," *Journal of Physical Chemistry B. ACS USA*, 106(6):4203-4213.
Mohr et al., 1997, "Application of Potential-Sensitive Fluorescent Dyes in Anion-and Cation-Sensitive Polymer Membranes," *Sensors and Actuators B, Elsevier Sequoia S.A., Lausanne, CH*, 39(1-3):239-245.
Bukhteeva et al., 1988, *Chemical Abstracts*, 108:48386.
International Search Report from PCT/US2004/013801 dated Sep. 15, 2004.
International Search Report dated Sep. 29, 2004.

*Primary Examiner* — Yong Chu
*Assistant Examiner* — Karen Cheng
(74) *Attorney, Agent, or Firm* — Applied Biosystems, LLC

(57) ABSTRACT

Fluorescent polymeric materials are disclosed comprising a polymeric particle and one or more lipid soluble rhodamine dyes, comprising the following core structure:

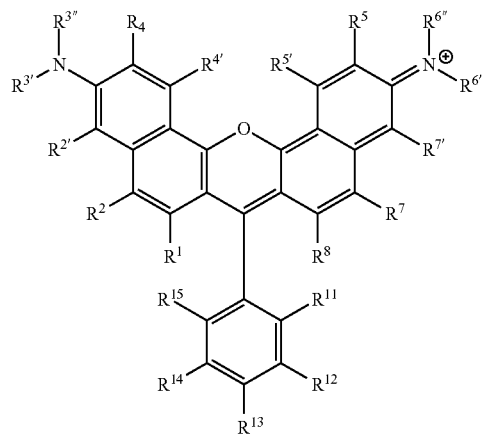

wherein $R^{11}$ and $R^{15}$ are each H or are each F or Cl; $R^{12}$, $R^{13}$, and $R^{14}$ are each H or are each F or Cl; and wherein at least one of $R^{3'}$, $R^{3''}$, $R^{6'}$ and $R^{6''}$ is a (C4-C20) alkyl. The materials are especially useful in the preparation of multicolored microparticles, especially multicolored polystyrene microparticle, for use in the multiplexed analysis of a plurality of analytes in a single sample. When excited by a light source, the materials give off a unique emission based on the nature, concentration and ratio of the dyes therein. Methods of preparing and using said materials are also disclosed.

15 Claims, 4 Drawing Sheets

(56) References Cited

U.S. PATENT DOCUMENTS

| | | |
|---|---|---|
| 5,847,162 A | 12/1998 | Lee et al. |
| 5,863,727 A | 1/1999 | Lee et al. |
| 5,936,087 A | 8/1999 | Benson et al. |
| 6,008,379 A | 12/1999 | Benson et al. |
| 6,020,481 A | 2/2000 | Benson et al. |
| 6,123,921 A | 9/2000 | Meade et al. |
| 6,143,570 A | 11/2000 | Alder et al. |
| 6,191,278 B1 | 2/2001 | Lee et al. |
| 6,229,055 B1 | 5/2001 | Klaubert et al. |
| 6,248,884 B1 | 6/2001 | Lam et al. |
| 6,268,222 B1 | 7/2001 | Chandler et al. |
| 6,372,907 B1 | 4/2002 | Lee et al. |
| 6,399,392 B1 | 6/2002 | Haugland et al. |
| 6,552,199 B1 | 4/2003 | Daltrozzo et al. |
| 6,998,493 B2 | 2/2006 | Banning et al. |

FOREIGN PATENT DOCUMENTS

| | | |
|---|---|---|
| DE | 199 26 377 A1 | 12/2000 |
| EP | 0 623 599 | 11/1994 |
| EP | 0892028 | 2/1999 |
| EP | 1394236 | 3/2004 |
| EP | 1422282 | 5/2004 |
| FR | 2 300 119 A1 | 9/1976 |
| GB | 1 454 815 | 2/1974 |
| JP | 48-096625 | 12/1973 |
| JP | 51-103129 | 9/1976 |
| JP | 60-25195 | 2/1985 |
| JP | 62-278570 | 12/1987 |
| JP | 02-127483 | 5/1990 |
| JP | 04-107559 | 4/1992 |
| JP | 11-279426 | 10/1999 |
| JP | 2000103975 | 4/2000 |
| JP | 2000239272 | 9/2000 |
| WO | 02/08245 | 1/2002 |
| WO | WO 02/08245 | 1/2002 |
| WO | 02/74388 | 9/2002 |
| WO | WO 02/074388 | 9/2002 |
| WO | WO 02/076397 | 10/2002 |
| WO | 02/076397 | 10/2003 |

FLUORESCENT POLYMERIC MATERIALS CONTAINING LIPID SOLUBLE RHODAMINE DYES

1. CROSS-REFERENCE TO RELATED APPLICATIONS

This application is a continuation of U.S. patent application Ser. No. 12/240,194, filed Sep. 29, 2008, which is a divisional of U.S. patent application Ser. No. 10/837,983, filed May 4, 2004, now U.S. Pat. No. 7,432,298, issued Oct. 7, 2008, which claims benefit under 35 U.S.C. §119(e) to U.S. Provisional Patent Application No. 60/469,030, filed May 9, 2003, entitled "Fluorescent Polymeric Materials Containing Lipid Soluble Rhodamine Dyes," the disclosures of which are herein incorporated by reference in their entirety.

2. BACKGROUND OF THE INVENTION

2.1. Field Of The Invention

Fluorescent polymeric particles that comprise a polymer and one or more lipid soluble rhodamine dyes are described herein.

2.2 Description of Related Art

Dyed polymeric materials are known in the art. However, there remains an ever present need to develop improved and more diverse dyed polymeric materials for use in, among other things, the multiplexed analysis of a plurality of analytes in a single assay. Specifically, there is a need for fluorescent polymeric materials that contain dyes that exhibit enhanced fluorescence, enhanced retention characteristics, and high photostability without significantly sacrificing other desirable properties. These and other needs are met by the materials described herein.

3. SUMMARY OF THE INVENTION

Fluorescent polymeric materials that comprise a polymer and one or more lipid-soluble rhodamine dyes are described herein. Optionally, one or more additional dyes may be present. Optionally, one or more additional materials may be present including biomolecules as well as compounds that aid in material separation such as paramagnetic compounds.

The polymer component may be any polymer that swells in an organic solvent or solvent system that is used to dissolve a lipid soluble rhodamine dye. Illustrative organic solvents include ethyl acetate and dichloromethane. In one embodiment, the polymer component is also sufficiently hydrophobic that it shrinks in alcoholic solvent, e.g., isopropanol.

Non-limiting examples of useful polymers include polymers polymerized from one or more substituted or unsubstituted versions of the following monomers: styrene; acrylate; alkyl acrylate; methacrylate; alkyl methacrylate; acrylonitrile; alkyl acrylonitrile; esters; acetates; amides; alcohols; isocyanates; acrolein; dimethylsiloxane; butadiene; isoprene; urethane; vinylacetate; vinylchloride; vinylpyridine; vinylbenzylchloride; vinyltoluene; vinylidene chloride; and mixtures thereof. The polymer may be crosslinked or uncrosslinked, and may take on virtually any shape or form, ranging from amorphous forms to structured forms like sheets, discs, pellets, beads, etc. In one embodiment, the polymer is a crosslinked polystyrene bead or particle.

The polymer component may be "activated" to include functional groups, such as carboxylate and/or amine groups, suitable for attaching the fluorescent polymeric material to another substance, such as, for example, biomolecules, haptens, drugs, poisons, vitamins, antigens and pathogens. Alternatively, the polymer component may include precursors of such functional groups that can be modified or transformed into such groups via chemical or other means. Activation of the polymer component to include such groups may occur before, during or after incorporation of the lipid soluble rhodamine dyes and/or other optional dyes.

The polymer component can include substances useful in the manipulation of the fluorescent polymeric material. For example, paramagnetic compounds may be present in, or on, the polymer that allow the polymer to be collected by a magnet. These compounds can be included during or after polymer formation. These substances can be physically entrapped in, or coated onto, the polymer component. In one embodiment, one or more paramagnetic compounds are physically entrapped within the polymer component during polymerization The polymer component may comprise one or more additional substances. For example, biomolecules, haptens, drugs, poisons, vitamins, antigens and pathogens can be absorbed, adsorbed or covalently attached to the polymer component which can, for example, enhance the polymer component's ability to capture an analyte. In one embodiment, one or more biomolecules are covalently attached to the polymer component at some point after the formation of the polymer component.

It will be evident to those skilled in the art that the polymers discussed above are readily available from a number of alternative commercial sources, e.g., Bangs Laboratories, Dynal, Sperotech, and Polyscience. Commercially available products that are available from these sources include, among other things, activated polymers, paramagnetic polymers, activated paramagnetic polymers, and polymers containing one or more biomolecules. For example, Bangs Laborites sells the following products: "plain (hydrophobic) polystyrene microspheres" of various sizes (catalog codes PS02N, PS03N, PS04N, PS05N, PS06N, PS07N, PS08N, PS00N); "carboxylate-modified microspheres" of various sizes (catalog codes PC02N, PC03N, PC04N, PC05N, PC06N, PC07N, PC08N and PC00N); "amino-modified microspheres" of various sizes (catalog codes PA02N, PA03N, PA04N, PA05N, PA06N, and PA00N); "classical magnetic microspheres" having carboxlic or amino functionality (catalog codes MC02N, MC03N, MC04N, MC05N, and MC00N); "encapsulated magnetic microspheres" with carboxylic and amino surface groups (catalog codes ME01N, ME02N, ME03N, and ME00N); and "protein-activated" or "protein-coated" mirospheres (catalog codes CM01N, CM02N, CM03N, CP01N, CP02N and CP03N). Similarly, Dynal sells Dynabeads®, a uniform, superparamagnetic, monodisperse polymer bead that can be uncoated or precoated with specific ligands. Dynabeads® are available in three different diameters, namely, 1 µm (Dynabeads®MyOne™ Streptavidin), 2.8 µm (Dynabeads® M-280 and Dynabeads® M-270) and 4.5 µm (Dynabeads® M-450 and Dynabeads® M-500).

The fluorescent polymeric materials additionally comprise one or more lipid-soluble rhodamine dyes. Rhodamines are a well-known class of dye characterized by three "main" features: a parent xanthene ring, an exocyclic amine group and an exocyclic imminium group. In most rhodamines, the exocyclic amine and imminium groups are attached to the 3- and 6-carbons of the parent xanthene ring. However, "extended rhodamines" are known in which the parent xanthene ring includes a 3,4- and/or a 5,6-benzo substituent (see, e.g., U.S. Pat. No. 6,248,884). In such "extended rhodamines" the exocyclic amine and imminium groups are attached to any present benzo substituents, as illustrated in U.S. Pat. No. 6,248,884.

As is well known, the parent xanthene ring of the rhodamines may be substituted at any and all of the aromatic carbons. Non-limiting examples of substituent groups that may be included in rhodamines at these positions include hydrogen, amino, hydroxy, alkoxy, mercapto, alkylthio, halo, haloalkyl, cyano, isocyano, cyanato, mercaptocyanato, nitroso, nitro, azido, sulfeno, sulfinyl, sulfino, sulfonyl, sulfonic acid, sulfonic ester, substituted and unsubstituted sulfinamoyl, substituted and unsubstituted sulfamoyl, aldehydes, ketones, carboxylic acid, carboxylic acid ester, amido, substituted or unsubstituted amidino, alkyl or heteroalkyl, aryl or heteroaryl, and arylalkyl or heteroarylalkyl. In addition, the substituents at the 2-, 4-, 5- and/or 7-carbon positions, or the corresponding portion of an extended rhodamine, may be fused to the nitrogen atom of their respective adjacent amine or imminium groups to form rhodamines in which the amine and/or imminium nitrogens are included in ring structures (see, e.g., U.S. Pat. Nos. 5,231,191, 5,410,053, 5,750,409, 5,847,162, 5,936,087, 6,008,379, 6,372,907, and 6,248,884). Rhodamines may also include benzo, naphtho or other polycyclic aryleno substituents fused to the 1,2 and/or 7,8 carbons, yielding benzo or naphtho rhodamines (see, e.g., U.S. Pat. Nos. 5,840,999, 5,847,162, 5,936,087, 6,008,379 and 6,248,884). The carbons of such benzo, naphtho or polycyclic aryleno substituents may be further substituted with, for example, one or more of the substituent groups described above.

Rhodamines may also be substituted at the 9-carbon (C-9 position) of the parent xanthene ring. In one class of rhodamines, the C-9 position is substituted with a phenyl group which may be further substituted or unsubstituted. Often, such rhodamines include a carboxylate or sulfonate group on the C-9 phenyl ortho to its point of attachment to the remainder of the ring. The remaining groups on the phenyl ring may be further substituted with substituent groups such as those previously described above. Many different types of rhodamines of this class are known and described (see, e.g., U.S. Pat. Nos. 5,231,191, 5,366,860, 5,410,053, 5,750,409, 5,840,999, 5,847,162, 5,936,087, 6,008,379 and 6,248,884).

In another class of rhodamines, the 9-carbon is substituted with a non-aromatic substituent, such as for example a hydrogen, alkyl, halo, haloalkyl or nitrile group. Rhodamines of this class are exemplified by the rhodamines described in U.S. Pat. Nos. 6,008,379 and 6,248,884.

Any of these rhodamines, if made lipid soluble, can be used in the fluorescent polymeric materials described herein. The degree of lipid solubility necessarily varies as a function of the polymer utilized, the aqueous solvent or solvent system employed in the assay in which the fluorescent polymeric material is used, and the conditions (e.g., time, temperature, pressure, pH, etc.) under which the assay is run. Suitable degrees of lipid solubility are easily determined by methods known in the art. For example, suitable lipid solubility can be determined by a partition test wherein a known quantity of dye in organic solvent is combined with the aqueous solvent or solvent system used in the assay. If a partition results and, under the conditions used in the assay, there is no appreciable crossing by the dye into the solvent or solvent system, then the dye is sufficiently lipid soluble. Put another way, the lipid soluble rhodamine dye should be sufficiently lipid soluble such that it is capable of being imbibed into the polymer when dissolved in an organic solvent or solvent system and, when the dyed polymer is subjected to the aqueous conditions of the assay, the dye should resist leaching out of the polymer to any degree that significantly impacts the fluorescent signature of the dye imbibed polymer or the results of the assay.

Generally, useful lipid-soluble rhodamines are rhodamines that are substituted at one or both of the exocyclic amine and/or imminium nitrogens with a lipophilic substituent group designed to impart the resultant rhodamine dye with lipophilic characteristics or properties. Thus, useful lipid-soluble rhodamines may include one or two lipophilic substituents at the exocyclic amine nitrogen and/or one or two lipophilic substituents at the exocyclic imminium nitrogen. The lipophilic substituents, whether attached to the same or different nitrogen atoms, may be the same or different. In one embodiment, the lipid-soluble rhodamine is a rhodamine in which the exocyclic amine and exocyclic imminium nitrogens are each substituted with identical lipophilic groups.

Lipid-soluble rhodamines may include lipophilic substitutents at other positions, as well. In certain embodiments, it may be desirable to "mask" polar substituents on a particular rhodamine with lipophilic substituent groups to alter the lipid-solubility of the resultant rhodamine. For example, rhodamines which include a C-9 phenyl substituted at the ortho position with a carboxylate or sulfonate group may be reacted with a lipophilic alcohol or amine, such as an alkyl, aryl or arylalkyl alcohol or amine, to yield an ortho ester or amide that contributes to the net lipophilic properties of the resultant rhodamine dye.

Lipophilic substituents are groups that impart the resultant rhodamine dye with lipophilic character or properties as denoted above. The nature of each lipophilic substituent is not critical, as long as the resultant rhodamine dye is lipid soluble. Non-limiting examples of suitable lipophilic substituents include unsubstituted (C4-C20) alkyls, (C5-C40) aryls, and (C6-C40) arylalkyls. Depending on the number of methylene and methine units in the lipophilic substituent, the lipophilic substituent may also include pendant or internal hydrophilic groups. For example, a lipophilic substitutent may include one or more internal heteroatoms, such as one or more internal O, S, N or NH groups. As another example, a lipophilic substituent may include one or more pendant polar or hydrophilic substituents, such as one or more pendant halogen, —OH, —SH, —NH$_2$, —C(O)OH, —C(O)NH$_2$ or other polar or hydrophilic groups. Thus, lipophilic substituents may also include substituted (C4-C20) alkyl, substituted (C5-C40) aryls and substituted (C6-C40) arylalkyls, as well as substituted and unsubstituted (C4-C20) heteroalkyl, substituted and unsubstituted (C5-C40) heteroaryls and substituted and unsubstituted (C6-C40) arylalkyls. As a specific example, if the rhodamine contains a C-9 phenyl ring, (C10-20) alkyl esters and alkyl amides are often employed in one or both of the positions ortho to the point of the phenyl ring's attachment. The number of internal or pendant polar or hydrophilic groups that may be included in a lipophilic substituent will depend upon, among other factors, the number of methylene or methine groups included in the lipophilic substitutent and the number of lipophilic substituents on the rhodamine dye. The nature and number of lipophilic groups necessary to make a rhodamine lipid soluble can vary from molecule to molecule, and will be apparent to those of skill in the art.

In one embodiment, the lipid-soluble rhodamine dyes useful in the fluorescent polymeric materials include any lipid-soluble dye comprising one of the following "core" structures:

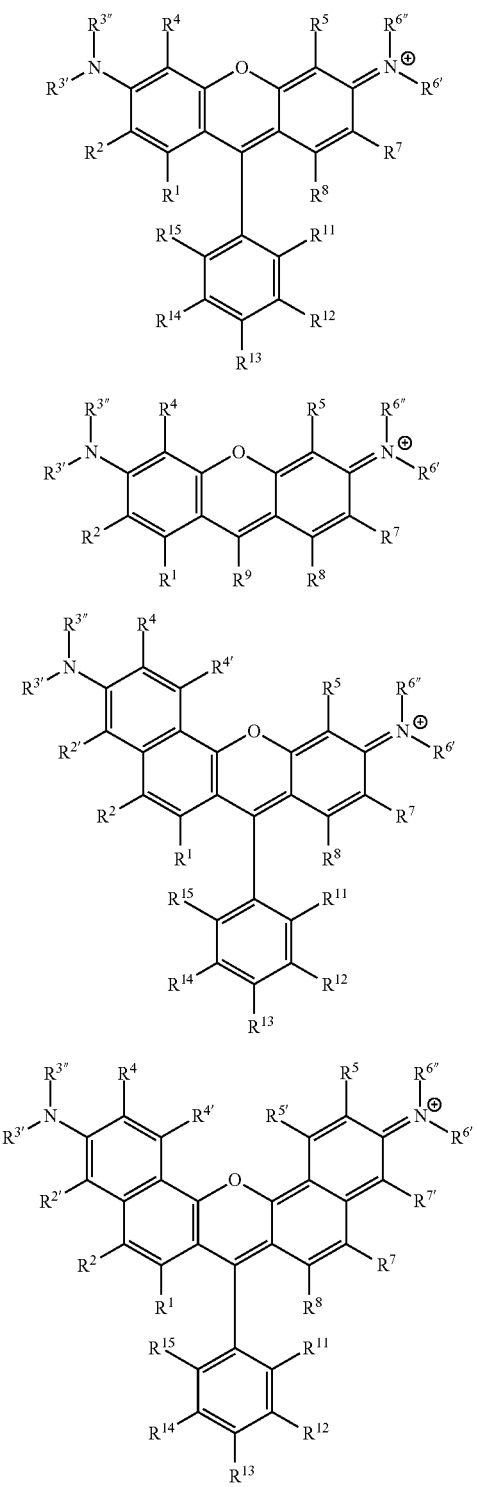

(I)

(II)

(III)

(IV)

where $R^1$ $R^2$, $R^{2'}$, $R^{3'}$, $R^{3''}$, $R^4$, $R^{4'}$, $R^{5'}$, $R^5$, $R^{6''}$, $R^{6'}$, $R^{7'}$, $R^7$, $R^8$, $R^9$, $R^{11}$ $R^{12}$, $R^{13}$, $R^{14}$ and $R^{15}$ are selected from hydrogen or the same or different substituent groups, at least one of $R^{3'}$, $R^{3''}$, $R^{6''}$ and $R^{6'}$ is a lipophilic substituent, and $R^9$ in structure (II) is a nonaromatic substituent. In one embodiment, all of the substituents, whether they represent $R^1$, $R^2$, $R^{2'}$, $R^{3'}$, $R^{3''}$, $R^4$, $R^{4'}$, $R^{5'}$, $R^5$, $R^{6''}$, $R^{6'}$, $R^{7'}$, $R^7$, $R^8$, $R^9$, $R^{11}$, $R^{12}$, $R^{13}$, $R^{14}$ or $R^{15}$, contain no more than 40 atoms. In another embodiment, the substituent groups at one or more of $R^2$, $R^{2'}$, $R^4$, $R^{4'}$, $R^{5'}$, $R^5$, $R^{7'}$, $R^7$, $R^9$, $R^{11}$, $R^{12}$, $R^{13}$, $R^{14}$, and $R^{15}$ are selected to "tune" the spectral features of the lipid-soluble rhodamine dye. Usually, for steric reasons, $R^1$ and $R^8$ in structures (I), (III) and (IV) are not simultaneously pendant or fused benzo, naphtho or polycyclic aryleno rings.

In embodiments in which the lipid-soluble rhodamine dye is attached to the polymer via a covalent linkage, one or more of $R^1$, $R^2$, $R^{2'}$, $R^4$, $R^5$, $R^7$, $R^8$, $R^{11}$, $R^{12}$, $R^{13}$, $R^{14}$ and $R^{15}$ may comprise a linking group suitable for effecting such covalent attachment. The linking group(s) may be attached directly to the remainder of the molecule, or may be spaced away from the molecule via a linker or spacer, as is well known in the art.

It has been discovered that certain types of C-9 phenyl substituted lipid soluble rhodamines have especially good fluorescent properties. These lipid soluble rhodamines depart from known C-9 phenyl substituted rhodamines in many ways, including the fact that they do not possess an ortho carboxylic acid or an ortho sulfonic acid moiety, or an amide, acid halide or salt derivative thereof. Often these lipid soluble rhodamines have symmetrical substitutions on the C-9 phenyl ring. In one embodiment, these lipid soluble rhodamine dyes comprise one of core structures (I), (III), and (IV) above where at least one of $R^{11}$ and $R^{15}$ are selected, independently of one another, from (C1-C20) alkyl or heteroalkyl, (C1-C20) alkoxy, halo, (C1-C20) haloalkyl, amino, mercapto, (C1-C20) alkylthio, cyano, isocyano, cyanato, mercaptocyanato, nitroso, nitro, azido, sulfeno, sulfinyl, and sulfino, and the remainder of $R^{12}$, $R^{13}$ and $R^{14}$ are selected, independently of one another, from hydrogen, (C1-C20) alkyl or heteroalkyl, (C1-C20) alkoxy, halo, (C1-C20) haloalkyl, amino, mercapto, (C1-C20) alkylthio, cyano, isocyano, cyanato, mercaptocyanato, nitroso, nitro, azido, sulfeno, sulfinyl, and sulfino. Alternatively, $R^{11}$ and $R^{15}$ are each the same substituent selected from (C1-C20) alkyl or heteroalkyl, (C1-C20) alkoxy, halo, (C1-C20) haloalkyl, amino, mercapto, (C1-C20) alkylthio, cyano, isocyano, cyanato, mercaptocyanato, nitroso, nitro, azido, sulfeno, sulfinyl, and sulfino, and the remainder of $R^{12}$, $R^{13}$ and $R^{14}$ are selected, independently of one another, from hydrogen, (C1-C20) alkyl or heteroalkyl, (C1-C20) alkoxy, halo, (C1-C20) haloalkyl, amino, mercapto, (C1-C20) alkylthio, cyano, isocyano, cyanato, mercaptocyanato, nitroso, nitro, azido, sulfeno, sulfinyl, and sulfino. In yet another embodiment, $R^{11}$ and $R^{15}$ are each the same substituent as just described and $R^{12}$, $R^{13}$ and $R^{14}$ are either unsubstituted or substituted in the same manner as $R^{11}$ and $R^{15}$. In still another embodiment, $R^{11}$ and $R^{15}$ are each the same halo group, such as chlorine or fluorine, and $R^{12}$, $R^{13}$ and $R^{14}$ are each hydrogen or the same halo group selected for $R^{11}$ and $R^{15}$.

The lipid soluble rhodamine dyes may be part of an energy transfer ("ET") network comprising, for example, two to four dyes covalently attached to one another that transfer energy to generate a longer Stoke's shift. One example of an ET network would be a fluorescence resonance energy transfer ("FRET") dye. In other words, the lipid soluble rhodamine dyes may be part of series of dyes that are covalently attached to one another wherein at least one of the dyes is a lipid soluble rhodamine. Linkages for covalently attaching rhodamine dyes to other dyes are known in the art, as are suitable locations for attachment to the rhodamine dyes (see, e.g., U.S. Pat. Nos. 5,800,996 and 5,863,727). In one embodiment, each dye in the energy transfer network is within 5 to 100 Å of the neighboring dye or dyes in the network to which it is covalently attached. In such embodiments, the lipid soluble rhodamine dye can be the donor, acceptor, or an intermediate dye in the network.

The lipid soluble rhodamine dyes may be used alone or in combination with one another. In addition, the lipid soluble rhodamine dyes may be used in combination with any other class of dye capable of fluorescing in the polymer employed. In one embodiment where the dyes are used in combination, the dyes are selected to impart the polymer material with a unique spectral signature or "bar code."

The aforementioned dyes are either imbibed into, or covalently bound to, the polymer. In one embodiment, the dyes are imbibed into the polymer without covalent attachment by introducing the dyes to the polymer in an organic solvent.

The fluorescent polymeric materials are useful in a wide variety of applications. For example, the fluorescent polymeric materials may be used as reference standards for fluorescence-based instruments, as biological tracers and in the detection and/or analysis of biological molecules. Numerous biological assays are known that employ biological or other molecules attached to solid supports. The fluorescent polymeric materials may be used as the solid support in any of these assays.

As a specific example, the fluorescent polymeric materials are especially beneficial in the formation of multicolored particles for use in multiplexed analysis of a plurality of analytes in a single assay. For example, a first polymeric particle or population of polymeric particles may be dyed with one or more fluorescent dyes, at least one of which is a lipid-soluble rhodamine dye as described above, at specified concentrations and ratios to create a first particle or particle population having a unique, discernable, fluorescence signature or "bar code." The first particle or particle population can then be modified to have a specific reactivity with one or more analytes. For example, the particle or particle population can be covalently attached to a molecule of interest, such as a potential drug candidate or a biological molecule such as an amino acid, a peptide, a protein, a nucleoside or nucleotide, an oligonucleotide, a polynucleotide, a carbohydrate or other molecule of interest. As specific examples, the first particle or particle population can be attached to an oligonucleotide which specifically hybridizes to a polynucleotide sequence of interest or, alternatively, to a peptide known or thought to inhibit an enzyme of interest. Thus, following modification, the spectral "bar code" of the first particle or first particle population corresponds to or correlates with the specific reactivity of the particle or particle population. In connection with the specific examples, the spectral "bar code" of the first particle or particle population corresponds to or correlates with the identity of the molecule of interest bound thereto.

The first particle or particle population may then be mixed with one or more additional particles or particle populations, each of which has a different, spectrally resolvable or discernable "bar code" due to differences in the identities, concentrations and/or ratios of the fluorescent dyes therein, and which correlate with different know reactivities. This forms a multicolored particle mixture in which the spectral "bar code" of a particular particle identifies the reactivity of the particle.

Depending upon the particular application, the particle mixture may be contacted with one or more analytes under conditions in which the analytes can interact with the particles. The analytes are typically molecules that are potentially capable of specifically binding the molecules attached to the particles. The analyte may be labeled with a fluorescent reporter dye that is spectrally resolvable from the "bar codes" of the particles. For example, if the bar code dyes emit in the red region of the spectrum, the analyte may be labeled with a fluorescent dye that emits in the green region of the spectrum.

Alternatively, the analyte may be unlabeled, or modified to include a recognition moiety recognized by another molecule (e.g., biotin or an antibody epitope) and the fluorescent reporter dye attached to a secondary molecule that specifically recognizes the analyte, the bound analyte or the recognition moiety. Following contact and washing to remove unbound analyte and/or secondary molecule, fluorescence from the reporter dye identifies the presence of bound analyte on particular particles. The fluorescent bar codes of these particles identifies their specific reactivities. In connection with the specific examples, the fluorescent bar code of a particular particle identifies the molecule bound thereto.

4. BRIEF DESCRIPTION OF THE DRAWINGS

Figure 4:
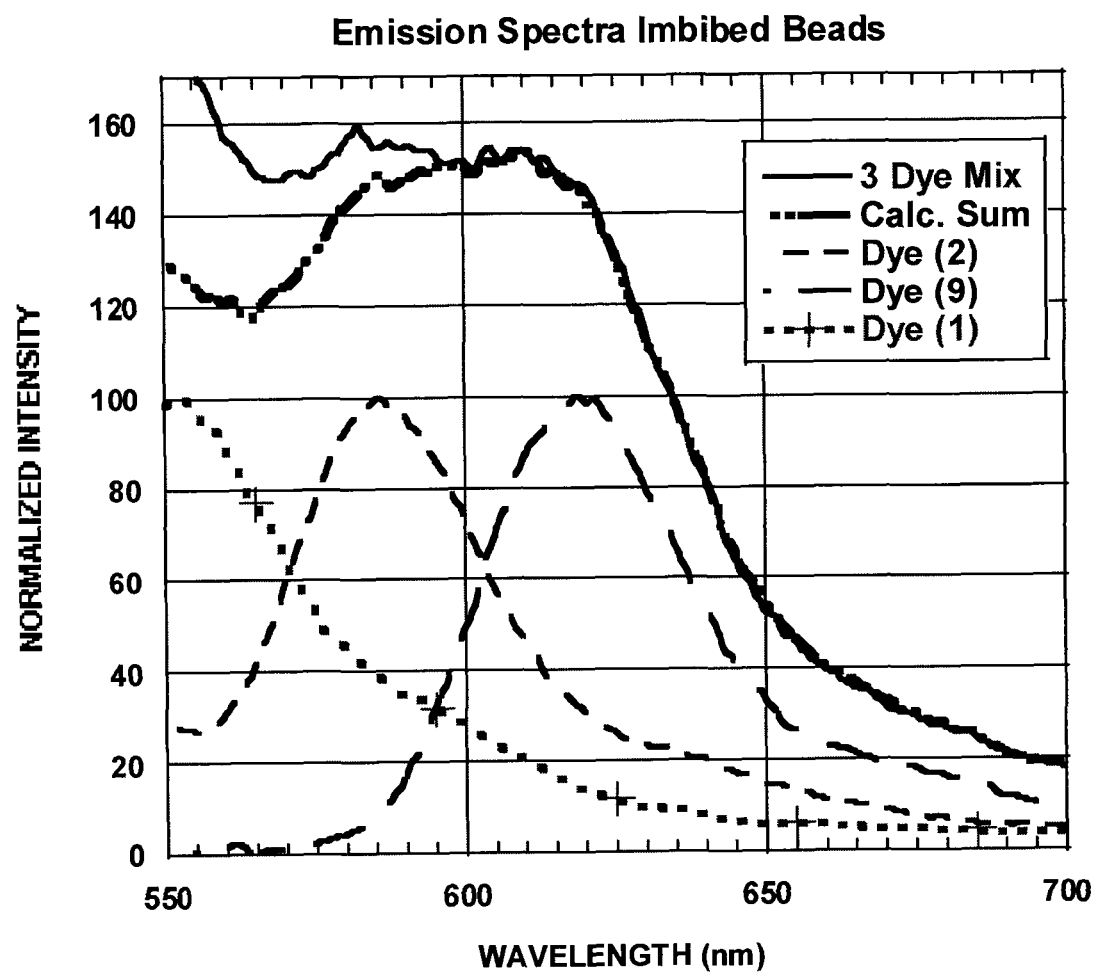

FIG. 4 provides a graph of normalized intensity versus wavelength for exemplary fluorescent dye imbibed beads.

5. DETAILED DESCRIPTION OF THE PREFERRED EMBODIMENTS

5.1 Numbering System

For the purposes of the present application, carbon atoms in the parent rhodamine rings, or extended versions thereof, are numbered in the manner illustrated below:

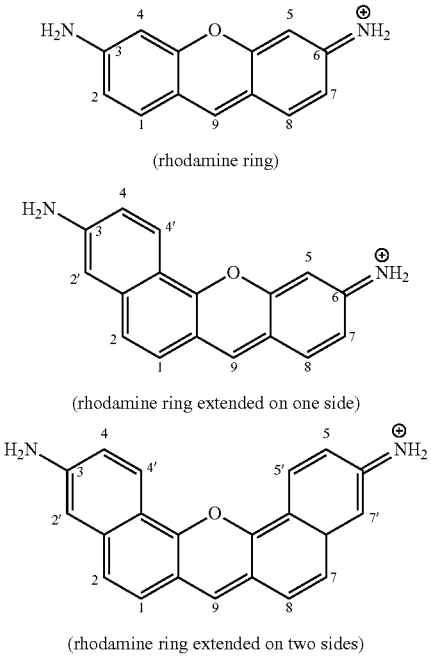

5.2 Definitions

As used herein, the following terms are intended to have the following meanings:

"Fluorescent Dye" or "Fluorescer" or "Fluorochrome" or "Fluorophore" as used interchangeably herein refer to molecules that absorb electromagnetic radiation at one wavelength and emit electromagnetic radiation at another wavelength in passing from a higher to a lower electronic state.

"Rhodamine" refers to any compound that comprises a parent rhodamine ring or an extended rhodamine ring, as set forth above, including any substituted versions of the same, wherein substitutions can be made at any one or all of the 1-, 2-, 2'-, 4-, 4'-, 5'-, 5-, 7'-, 7-, 8- and 9-carbons and/or at any one or both of the exocyclic amino and imino nitrogens.

"Polymer," as used herein, refers not only to homopolymers but also to copolymers, terpolymers, and the like, whether branched or linear and whether crosslinked or uncrosslinked.

"Poly-," when used as a prefix in the name of a polymer, refers to a polymer made up in the majority of the monomer or monomers that follow the prefix.

"Particles" as used herein refers to solid masses that are spherical or irregular in shape.

"Particle size" or "Particle Diameter" as used interchangeably herein refers to mean particle diameter. As known in the art, there are many methods for measuring particle size including sieving, centrifugation, light scattering, image analysis, electrozone sensing, and x-ray scattering. Each method can produce different results. Accordingly, whenever a particle size range is specified in this description it refers to a particle size as measured by light scattering.

"Microparticles" as used herein refer to particles having a particle size anywhere between 0.01 to 1000 micrometers as measured by light scattering.

"Biomolecule" as used herein refers to a molecule of a type typically found in a biological system, whether such molecule is naturally occurring or the result of some external disturbance of the system (e.g., a disease, poisoning, genetic manipulation, etc.), as well as synthetic analogs and derivatives thereof. Non-limiting examples of biomolecules include amino acids (naturally occurring or synthetic), peptides, polypeptides, glycosylated and unglycosylated proteins (e.g., polyclonal and monoclonal antibodies, receptors, interferons, enzymes, etc.), nucleosides, nucleotides, oligonucleotides (e.g., DNA, RNA, PNA oligos), polynucleotides (e.g., DNA, cDNA, RNA, etc.), carbohydrates, hormones, haptens, steroids, toxins, etc. Biomolecules may be isolated from natural sources, or they may be synthetic. "Analyte" is a molecule or substance to be measured or assayed. Depending on the nature of the assay, an analyte can be either a molecule or a substance attached to the polymer or a molecule or substance in solution.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C20) alkyl.

"Heteroalkyl," by itself or as part of another substituent refers to an alkyl in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR$^m$—, —P(O)O—, —S(O)—, —S(O)$_2$—, —S(O)NR$^m$—, —S(O)$_2$NR$^m$—, and the like, including combinations thereof, where each R$^m$ is independently hydrogen or (C1-C6) alkyl.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes 1-fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —$OR''$, "alkylamine" refers to a group of the formula —$NHR''$ and "dialkylamine" refers to a group of the formula —$NR''R''$, where each $R''$ is independently an alkyl. As another example, "haloalkoxy" or "haloalkyloxy" refers to a group of the formula —$OR^p$, where $R^p$ is a haloalkyl.

5.3 The Components Generally

The present invention provides new types of fluorescent polymeric materials. The fluorescent polymeric materials comprise a polymer that is either imbibed with, or covalently attached to, one or more lipid soluble rhodamine dyes and, optionally, one or more additional dyes. The polymer may be activated to include functional groups suitable for attaching another substance such as a biomolecule. Alternatively, the polymer component may include precursors of such functional groups that can be modified or transformed into such groups via chemical or other means.

The fluorescent polymeric materials can also include one or more other substances, such as biomolecules, haptens, drugs, poisons, vitamins, antigens and pathogens, that are absorbed, adsorbed or covalently attached to the polymer. These substances can be added, for example, to enhance the polymer component's ability to capture an analyte. Additional substances that may be part of the fluorescent polymeric materials include compounds that assist in the manipulation of the fluorescent polymeric material. For example, paramagnetic compounds can be included that permit the fluorescent polymeric material to be collected by a magnet. All of these substances can be physically entrapped within, imbibed into, covalently attached to, or coated onto the polymer component.

5.4 The Polymer Component

The polymer component may be any polymer that can be dissolved in, or made to swell in, an organic solvent or solvent system that is used to dissolve a lipid soluble rhodamine dye. Illustrative organic solvents include ethyl acetate and/or dichloromethane. In one embodiment, the polymer component is sufficiently hydrophobic that it also shrinks in alcoholic solvent, e.g., isopropanol. This assists, for example, in entrapping previously imbibed lipid soluble rhodamine dyes.

Non-limiting examples of polymer components useful in the fluorescent polymeric materials of the instant invention are polymers polymerized from substituted or unsubstituted versions of the following monomers: styrene; acrylate; alkyl acrylate; methacrylate; alkyl methacrylate; acrylonitrile; alkyl acrylonitrile; esters; acetates; amides; alcohols; acrolein; dimethylsiloxane, butadiene, isoprene, urethane, vinylacetate, vinylchloride, vinylpyridine, vinylbenzylchloride; vinyltoluene; vinylidene chloride; and mixtures thereof. Specific non-limiting examples of suitable polymers include polystyrene, brominated polystyrene, poly(methyl methacrylate), poly(acrylonitrile), polyacrolein, poly(dimethyl siloxane), polybutadiene, polyisoprene, polyurethane, poly(vinyl acetate), poly(vinyl chloride), poly(vinyl pyridine), poly(vinyl benzylchloride), poly(vinyl toluene), poly(vinylidene chloride) and poly(divinyl benzene). Other suitable polymers are known in the art and disclosed, for instance, in U.S. Pat. No. 6,268,222, which is incorporated herein by reference. In one embodiment of the invention, the polymer is a polystyrene homopolymer or a copolymer of styrene polymerized with one or more other monomers, such as acrylic acid.

The polymer can be crosslinked or uncrosslinked. The identity and amount of crosslinking agents that can be employed varies based on the selection of the particular polymer in a manner that is readily evident to those skilled in the art. Crosslinking agents are generally used in amounts ranging from about 0.01 to about 50 percent by weight of the polymer. In one embodiment, crosslinking agents are employed in amounts ranging from 0.05 to 20 percent by weight of the polymer. In another embodiment, crosslinking agents are employed in amounts ranging from 1 to 5 percent by weight of the polymer. The more crosslinking agent utilized, the less the polymer is able to swell. Illustrative non-limiting examples of suitable crosslinking agents include divinyl benzene, ethylene glycol dimethacrylate, trimethylol propane trimethacrylate, and N,N'-methylene-bis-acrylamide, and the like. Basically, any polyfunctional reactive agent can be utilized as a crosslinking agent. In one embodiment, the polymer is a hydrophobic copolymer of styrene, acrylic acid, and a polyvinyl crosslinking agent. Non-limiting examples of such polymers include those polymerized from 85% or more styrene, 0.01 to 15% acrylic acid, and 0.01 to 5% polyvinyl crosslinking agent. Illustrative copolymers are styrene-acrylic acid-divinyl benzene (89:10:1 molar ratio).

The polymer may take on virtually any shape or form, ranging from amorphous forms to structured forms like sheets, discs, pellets, beads, etc. In one embodiment, the polymer forms particles, and ideally microparticles, which substantially retain their shape in aqueous solvent so that they are useful in biological assays. By microparticles it is meant that the particles have a mean diameter ranging from about 0.01 to about 1000 micrometers. Although the microparticles can have any particle size within this range, in one embodiment the particles range in size from about 0.1 to about 500 micrometers. Alternatively, the particles may range in size from about 1 to about 200 micrometers. In another embodiment the particles range in size from about 1 to about 12 micrometers. In yet another embodiment, the particle size is from about 1 to about 5 micrometers. The polymer particles may be uniform or of variable size and shape. Preferably, the polymer particles are roughly spherical and of a generally uniform diameter.

Optionally, the polymer component can be "activated" to include a reactive functionality (e.g., NHS-ester) capable of forming a chemical attachment to another substance. Alternatively, the polymer component can be "activated" to include groups that have a functionality (e.g., carboxylic acid) that are known precursors to reactive functionalities capable of forming a chemical attachment to another substance. Non-limiting examples of other substances for attachment include biomolecules, drugs, poisons, vitamins, antigens and pathogens. Activation can be accomplished either by copolymerizing or grafting functional monomers into the polymer during polymer formation or by chemically modifying the polymer after formation. The reactive groups may be nucleophilic and/or electrophilic functional groups. Non-limiting examples of suitable nucleophilic reactive groups include any one or a combination of the following: amines/anilines; alcohols/phenols; thiols; hydrazines; and hydroxylamines. Non-limiting examples of suitable electrophilic reactive groups include any one or a combination of the following: pentafluorophenyl ester; NHS-ester; acrylamides; acyl azides; acyl halides; acyl nitriles; aldehydes or ketones; alkyl halides; alkyl sulfonates; anhydrides; aryl halides; aziridines; boronates; carboxylic acids; carbodiimides; diazoalkenes; epoxides; haloacetamides; halotriazines; imido esters; isocyanates; isothiocyanates; maleimides; phorphoramidites; silyl halides; sulfonate esters; and sulfonyl halides.

The identity of any particular activating group will depend upon the particular application, for example upon the identity of the molecules to be attached thereto, and will be apparent to those of skill in the art. For example, polymers activated with carboxyl groups are especially suitable for attachment to the primary amine groups of proteins or amine-modified oligonucleotides. Such carboxyl groups can be introduced into the polymer chain through reactive comonomers such as (meth)acrylic acid. In addition, polymers containing groups such as diamines, dihydrazides, mercaptoalkylamines and dimercaptans are useful for attaching various drugs or enzymes.

The nature of the active groups can be selected to manipulate various characteristics of the polymer surface. For example, if desired, active groups can be selected to make the polymer surface more hydrophilic.

As will be further detailed, the polymer can include paramagnetic compounds such as magnetite ($Fe_3O_4$). These compounds can be coated onto the polymer surface during or after formation and/or entrapped into the polymer during polymerization. For example, one method of incorporating paramagnetic compounds into the polymer is to form a core of a core shell polymer, coat the core with a paramagnetic compound, and then form the shell of the core shell polymer over the paramagnetic compound, thereby entrapping the paramagnetic compound within the finished polymer.

As will also be further detailed, the polymer component can comprise one or more additional substances. For example, biomolecules, haptens, drugs, poisons, vitamins, antigens and pathogens can be absorbed, adsorbed or covalently attached to the polymer component which can, for example, enhance the polymer component's ability to capture an analyte. In one embodiment, one or more of biomolecules are covalently attached to the polymer component at some point after the formation of the polymer component.

It will be evident to those skilled in the art that the polymers discussed above are readily available from a number of alternative commercial sources, e.g., Bangs Laboratories, Dynal, Sperotech, and Polyscience. Commercially available products that are available from these sources include, among others, activated polymers, paramagnetic polymers, activated paramagnetic polymers, and polymers containing one or more biomolecules. For example, Bangs Laboraties sells the following products: "plain (hydrophobic) polystyrene microspheres" of various sizes (catalog codes PS02N, PS03N, PS04N, PS05N, PS06N, PS07N, PS08N, PS00N); "carboxylate-modified microspheres" of various sizes (catalog codes PC02N, PC03N, PC04N, PC05N, PC06N, PC07N, PC08N and PC00N); "amino-modified microspheres" of various sizes (catalog codes PA02N, PA03N, PA04N, PA05N, PA06N, and PA00N); "classical magnetic microspheres" having carboxlic or amino functionality (catalog codes MC02N, MC03N, MC04N, MC05N, and MC00N); "encapsulated magnetic microspheres" with carboxylic and amino surface groups (catalog codes ME01N, ME02N, ME03N, and ME00N); and "protein-activated" or "protein-coated" mirospheres (catalog codes CM01N, CM02N, CM03N, CP01N, CP02N and CP03N). Similarly, Dynal sells Dynabeads®, a uniform, superparamagnetic, monodisperse polymer bead that can be uncoated or precoated with specific ligands. Dynabeads® are available in three different diameters, namely, 1 μm (Dynabeads® MyOne™ Streptavidin), 2.8 μm (Dynabeads® M-280 and Dynabeads® M-270) and 4.5 μm (Dynabeads® M-450 and Dynabeads® M-500).

5.5 Lipid Soluble Rhodamine Dyes Generally

The polymer component is imbibed or swelled with, or dissolved in, a solution of one or more lipid soluble rhodamine dyes and, optionally, one or more additional dyes. Alternatively, the lipid soluble rhodamine dyes can be covalently attached to the polymer.

Rhodamines are a well-known class of dye characterized by three "main" features: a parent xanthene ring, an exocyclic amine group and an exocyclic imminium group. In most rhodamines, the exocyclic amine and imminium groups are attached to the 3- and 6-carbons of the parent xanthene ring.

However, "extended rhodamines" are known in which the parent xanthene ring includes a 3,4- and/or a 5,6-benzo substituent. In this regard, U.S. Pat. No. 6,248,884 is hereby incorporated by reference. In such "extended rhodamines" the exocyclic amine and imminium groups are attached to any present 3,4- and/or 5,6-benzo substituents.

The parent xanthene ring of the rhodamines may be substituted at the 1-, 2-, 2'-, 4-, 4'-, 5-, 5'-, 7-, 7'- and 8-carbon positions. Non-limiting examples of substituent groups that may be included in rhodamines at these positions include hydrogen, amino, hydroxy, alkoxy, mercapto, alkylthio, halo, haloalkyl, cyano, isocyano, cyanato, mercaptocyanato, nitroso, nitro, azido, sulfeno, sulfinyl, sulfino, sulfonyl, sulfonic acid, sulfonic ester, substituted and unsubstituted sulfinamoyl, substituted and unsubstituted sulfamoyl, aldehydes, ketones, carboxylic acid, carboxylic acid ester, amido, substituted or unsubstituted amidino, alkyl or heteroalkyl, aryl or heteroaryl, and arylalkyl or heteroarylalkyl.

In addition, the substituents at the 2- or 2'-, 4-, 5- and/or 7- or 7'-carbon positions may be fused to the nitrogen atom of their respective adjacent amine or imminium groups to form rhodamines in which the amine and/or imminium nitrogens are included in ring structures. In this regard, U.S. Pat. Nos. 5,231,191, 5,410,053, 5,750,409, 5,847,162, 5,936,087, 6,008,379, 6,372,907, and 6,248,884 are hereby incorporated by reference. Rhodamines may also include benzo, naphtho or other polycyclic aryleno substituents fused to the 1,2 and/or 7,8 carbons, yielding benzo or naphtho rhodamines. In this regard, U.S. Pat. Nos. 5,840,999, 5,847,162, 5,936,087, 6,008,379 and 6,248,884 are hereby incorporated by reference. The carbons of such benzo, naphtho or polycyclic aryleno substituents may be further substituted with, for example, one or more of the substituent groups described above.

Rhodamines may also be substituted at the 9-carbon (C-9 position) of the parent xanthene ring. In one class of rhodamines, the C-9 position is substituted with a phenyl group which may be further substituted or unsubstituted. Often, such rhodamines include a carboxylate or sulfonate group positioned ortho to the point of attachment. The remaining groups on the phenyl ring may be unsubstituted or substituted with substituent groups such as those previously described above. Rhodamines of this class are known and described in U.S. Pat. Nos. 5,231,191, 5,366,860, 5,410,053, 5,750,409, 5,840,999, 5,847,162, 5,936,087, 6,008,379 and 6,248,884, all of which are hereby incorporated by reference.

In another class of rhodamines, the C-9 position is substituted with a non-aromatic substituent, such as a hydrogen, alkyl, halo, haloalkyl or nitrile group. Rhodamines of this class are described in U.S. Pat. Nos. 6,008,379 and 6,248,884, both of which are hereby incorporated by reference.

Any of these rhodamines, if made lipid soluble, can be used in the fluorescent polymeric materials described herein. The degree of lipid solubility necessarily varies as a function of the polymer utilized, the aqueous solvent or solvent system employed in the assay in which the fluorescent polymeric material will be used, and the conditions (e.g., time, temperature, pressure, pH, etc.) under which the assay is run. Suitable degrees of lipid solubility are easily determined by methods known in the art. For example, suitable lipid solubility can be determined by a partition test wherein a known quantity of the dye in organic solvent is combined with the solvent or solvent system used in the assay. If a partition results and, under the conditions used in the assay, there is no appreciable crossing by the dye into the solvent or solvent system, then the dye is sufficiently lipid soluble. Put another way, the lipid soluble rhodamine dye should be sufficiently lipid soluble such that it is capable of being imbibed into the polymer when dissolved in an organic solvent or solvent system and, when the dyed polymer is subjected to the aqueous conditions of the assay, the dye should resist leaching out of the polymer to any degree that significantly impacts the fluorescent signature of the dye imbibed polymer or the results of the assay.

Generally, useful lipid-soluble rhodamines are rhodamines that are substituted at one or both of the exocyclic amine and/or imminium nitrogens with a lipophilic substituent group designed to impart the resultant rhodamine dye with lipophilic characteristics or properties. Thus, useful lipid-soluble rhodamines may include one or two lipophilic substituents at the exocyclic amine nitrogen and/or one or two lipophilic substituents at the exocyclic imminium nitrogen. The lipophilic substituents, whether attached to the same or different nitrogen atoms, may be the same or different. In one embodiment, the lipid-soluble rhodamine is a rhodamine in which the exocyclic amine and exocyclic imminium nitrogens are each substituted with identical lipophilic groups.

Lipid-soluble rhodamines may include lipophilic substitutents at other positions, as well. In certain embodiments, it may be desirable to "mask" polar substituents on a particular rhodamine with lipophilic substituent groups to alter the lipid-solubility of the resultant rhodamine. For example, rhodamines which include a C-9 phenyl substituted at the ortho position with a carboxylate or sulfonate group may be reacted with a lipophilic alcohol or amine, such as an alkyl, aryl or arylalkyl alcohol or amine, to yield an ortho ester or amide that contributes to the net lipophilic properties of the resultant rhodamine dye.

Lipophilic substituents are groups that impart the resultant rhodamine dye with lipophilic character or properties as denoted above. The nature of each lipophilic substituent is not critical, as long as the resultant rhodamine dye is lipid soluble. Non-limiting examples of suitable lipophilic substituents include unsubstituted (C4-C20) alkyls, (C5-C40) aryls, and (C6-C40) arylalkyls. Depending on the number of methylene and methine units in the lipophilic substituent, the lipophilic substituent may also include pendant or internal hydrophilic groups. For example, a lipophilic substituent may include one or more internal heteroatoms, such as one or more internal O, S, N or NH groups. As another example, a lipophilic substituent may include one or more pendant polar or hydrophilic substituents, such as one or more pendant halogen, —OH, —SH, —NH$_2$, —C(O)OH, —C(O)NH$_2$ or other polar or hydrophilic groups. Thus, lipophilic substituents may also include substituted (C4-C20) alkyl, substituted (C5-C40) aryls and substituted (C6-C40) arylalkyls, as well as substituted and unsubstituted (C4-C20) heteroalkyl, substituted and unsubstituted (C5-C40) heteroaryls and substituted and unsubstituted (C6-C40) arylalkyls. As a specific example, if the rhodamine contains a C-9 phenyl ring, (C10-20) alkyl esters and alkyl amides are often employed in one or both of the positions ortho to the point of the phenyl ring's attachment. The number of internal or pendant polar or hydrophilic groups that may be included in a lipophilic substituent will depend upon, among other factors, the number of methylene or methine groups included in the lipophilic substitutent and the number of lipophilic substituents on the rhodamine dye. The nature and number of lipophilic groups necessary to make a rhodamine lipid soluble can vary from molecule to molecule, and will be apparent to those of skill in the art.

In one embodiment, lipid-soluble rhodamine dyes useful in the fluorescent polymeric materials of the invention comprise one of the following "core" structures:

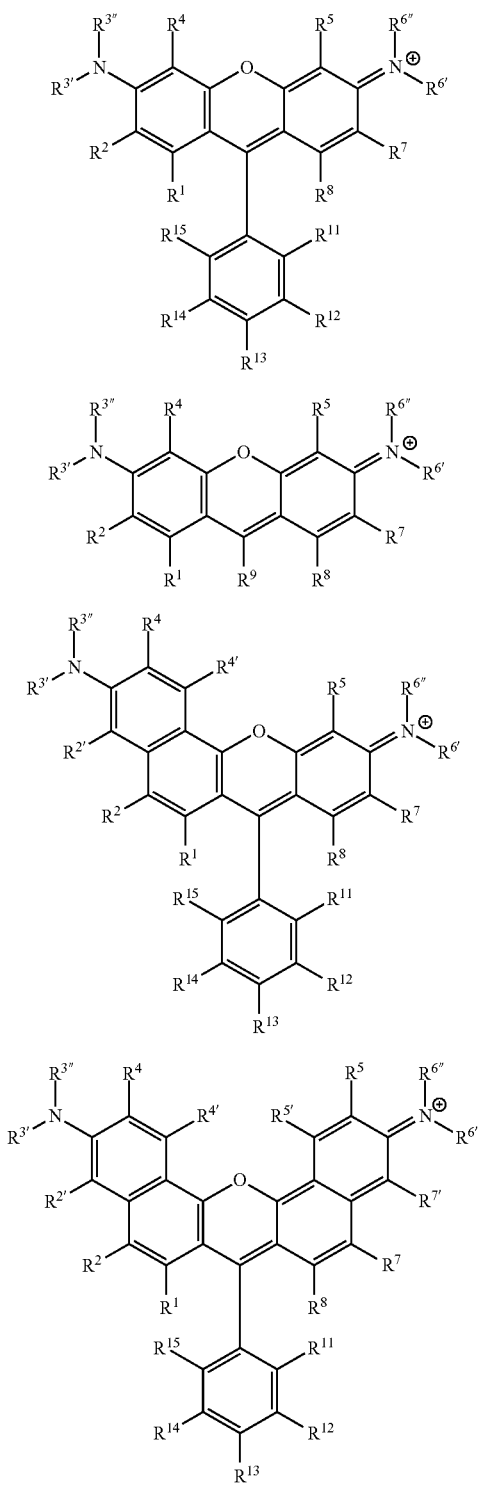

$R^1$ $R^2$, $R^{2'}$, $R^{3'}$, $R^{3'''}$, $R^4$, $R^{4'}$, $R^{5'}$, $R^5$, $R^{6'''}$, $R^{6'}$, $R^{7'}$, $R^7$, $R^8$, $R^9$, $R^{11}$ $R^{12}$, $R^{13}$, $R^{14}$ and $R^{15}$ are selected from hydrogen or the same or different substituent groups; at least one of $R^{3'}$, $R^{3'''}$, $R^{6'''}$ and $R^{6'}$ is a lipophilic substituent; and $R^9$ in structure (II) is a nonaromatic substituent. In one embodiment, all of the substituents, whether they represent $R^2$, $R^{2'}$, $R^{3'}$, $R^{3'''}$, $R^4$, $R^{4'}$, $R^{5'}$, $R^5$, $R^{6'''}$, $R^{6'}$, $R^{7'}$, $R^7$, $R^8$, $R^9$, $R^{11}$, $R^{12}$, $R^{13}$, $R^{14}$ or $R^{15}$, contain no more than 40 atoms. In another embodiment all of the substituents, whether they represent $R^2$, $R^{2'}$, $R^{3'}$, $R^{3'''}$, $R^4$, $R^{4'}$, $R^{5'}$, $R^5$, $R^{6'''}$, $R^{6'}$, $R^{7'}$, $R^7$, $R^8$, $R^9$, $R^{11}$, $R^{12}$, $R^{13}$, $R^{14}$ or $R^{15}$, contain no more than 25 atoms.

Lipid solubility is imparted to the rhodamine dyes of structures (I), (II), (III) and (IV) through the combination of substituents selected. Lipophilic substituents at of $R^{3'}$, $R^{3'''}$, $R^{6'''}$ and $R^{6'}$ are especially useful in this regard. In one embodiment, at least one $R^{3'}$, $R^{3'''}$, $R^{6'''}$ and $R^{6'}$ is lipophilic. In another embodiment, at least two of $R^{3'}$, $R^{3'''}$, $R^{6'''}$ and $R^{6'}$ are lipophilic substituents. In yet another embodiment, all four of $R^{3'}$, $R^{3'''}$, $R^{6'''}$ and $R^{6'}$ are lipophilic substituents. These lipophilic substituents may be the same or different. Non-limiting examples of suitable lipophilic substituents include unsubstituted (C4-C20) alkyls, (C5-C40) aryls, and (C6-C40) arylalkyls. Depending on the number of methylene and methine units in the lipophilic substituent, the lipophilic substituent may also include pendant or internal hydrophilic groups. For example, a lipophilic substitutent may include one or more internal heteroatoms, such as one or more internal O, S, N or NH groups. As another example, a lipophilic substituent may include one or more pendant polar or hydrophilic substituents, such as one or more pendant halogen, —OH, —SH, —NH$_2$, —C(O)OH, —C(O)NH$_2$ or other polar or hydrophilic groups. Thus, lipophilic substituents may also include substituted (C4-C20) alkyl, substituted (C5-C40) aryls and substituted (C6-C40) arylalkyls, as well as substituted and unsubstituted (C4-C20) heteroalkyl, substituted and unsubstituted (C5-C40) heteroaryls and substituted and unsubstituted (C6-C40) arylalkyls.

The fluorescent properties of the lipid soluble rhodamine dyes can be tuned by the selection of different substituents, as is well known in the art. Especially beneficial substituents for tuning the lipid soluble rhodamine dyes include the moieties on the 9-carbon, namely, $R^9$, $R^{11}$, $R^{12}$, $R^{13}$, $R^{14}$ and $R^{15}$. The $R^2$, $R^{2'}$, $R^4$, $R^{4'}$ $R^{5'}$, $R^5$, $R^{7'}$ and $R^7$ substituents are also beneficial toward tuning the spectral properties of the dyes.

Symmetry is an important factor in selecting optimal dyes. Accordingly, it is desirable, but not necessary, for the lipid soluble rhodamine dyes to have identical $R^{3'}$ and $R^{6'}$ substituents and/or identical $R^{3'''}$ and $R^{6'''}$ substituents and/or identical $R^4$ and $R^5$ substituents. Similarly, it is desirable, but not necessary, for the dyes to have identical $R^1$ and $R^8$ substituents and/or identical $R^2$ and $R^7$ substituents. Finally, with respect to structure (II), it is desirable, but not necessary, for the benzo, naphtho or polycyclic aryleno groups that bridge $R^1$ and $R^2$ to be identical to the benzo, naphtho or polycyclic aryleno groups that bridge $R^7$ and $R^8$. The presence of one or more, and especially all, of these symmetries facilitates the production of a strong emission spectrum with a narrow full width half max.

Typically, $R^1$ and $R^8$ in structures (I), (III) and (IV) are not, simultaneously, pendant or fused benzo, naphtho or polycyclic aryleno groups. The simultaneous presence of two relatively rigid aromatic rings immediately next to the 9-carbon may generate steric hinderances when the C-9 position is substituted with a substituted or unsubstituted phenyl substituent. Such steric hinderance is not a concern for structure (II), where $R^9$ is, by definition, a nonaromatic substituent.

Often, with respect to structures (I), (III) and (IV), the dyes are more limited if the polymer utilized is neither activated nor in particulate form. Specifically, in such scenarios, if $R^{3'''}$ and $R^{6'''}$ are each phenyl or substituted phenyl and if $R^{3'}$ and $R^{6'}$ are each hydrogen, then at least two of $R^{11}$, $R^{12}$, $R^{13}$, $R^{14}$ and $R^{15}$ must be other than hydrogen.

It has been discovered that certain types of C-9 phenyl substituted lipid soluble rhodamines have especially good fluorescent properties. These lipid soluble rhodamines depart from known C-9 phenyl substituted rhodamines in many ways, including the fact that they do not possess an ortho carboxylic acid or an ortho sulfonic acid moiety, or an amide, acid halide or salt derivative thereof. Often these lipid soluble rhodamines have symmetrical substitutions on the C-9 phenyl ring. In one embodiment, these lipid soluble rhodamine dyes comprise one of core structures (I), (III), and (IV) above where at least one of $R^{11}$ and $R^{15}$ are selected, independently of one another, from (C1-C20) alkyl or heteroalkyl, (C1-C20) alkoxy, halo, (C1-C20) haloalkyl, amino, mercapto, (C1-C20) alkylthio, cyano, isocyano, cyanato, mercaptocyanato, nitroso, nitro, azido, sulfeno, sulfinyl, and sulfino, and the remainder of $R^{12}$, $R^{13}$ and $R^{14}$ are selected, independently of one another, from hydrogen, (C1-C20) alkyl or heteroalkyl, (C1-C20) alkoxy, halo, (C1-C20) haloalkyl, amino, mercapto, (C1-C20) alkylthio, cyano, isocyano, cyanato, mercaptocyanato, nitroso, nitro, azido, sulfeno, sulfinyl, and sulfino. Alternatively, $R^{11}$ and $R^{15}$ are each the same substituent selected from (C1-C20) alkyl or heteroalkyl, (C1-C20) alkoxy, halo, (C1-C20) haloalkyl, amino, mercapto, (C1-C20) alkylthio, cyano, isocyano, cyanato, mercaptocyanato, nitroso, nitro, azido, sulfeno, sulfinyl, and sulfino, and the remainder of $R^{12}$, $R^{13}$ and $R^{14}$ are selected, independently of one another, from hydrogen, (C1-C20) alkyl or heteroalkyl, (C1-C20) alkoxy, halo, (C1-C20) haloalkyl, amino, mercapto, (C1-C20) alkylthio, cyano, isocyano, cyanato, mercaptocyanato, nitroso, nitro, azido, sulfeno, sulfinyl, and sulfino. In yet another embodiment, $R^{11}$ and $R^{15}$ are each the same substituent as just described and $R^{12}$, $R^{13}$ and $R^{14}$ are either unsubstituted or substituted in the same manner as $R^{11}$ and $R^{15}$. In still another embodiment, $R^{11}$ and $R^{15}$ are each the same halo group, such as chlorine or fluorine, and $R^{12}$, $R^{13}$ and $R^{14}$ are each hydrogen or the same halo group selected for $R^{11}$ and $R^{15}$.

5.6 Structure (I) Dyes

In one embodiment, the lipid soluble rhodamine dyes comprise core structure (I) and, additionally, the substituents therein are defined as follows:

$R^1$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^1$ is taken together with $R^2$ form part of a benzo, naptho or polycyclic aryleno group which is optionally substituted with one or more of the same or different $R^a$ or suitable $R^b$ groups;

$R^2$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^2$ is taken together with $R^1$ to form part of a benzo, naptho or polycyclic aryleno group which is optionally substituted with one or more of the same or different $R^a$ or suitable $R^b$ groups, or, alternatively, $R^2$ is taken together with $R^{3'}$ to form a 5- or 6-membered ring which is optionally substituted with one or more of the same or different $R^a$ or suitable $R^b$ groups;

$R^{3'}$ is selected from (C4-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively, $R^{3'}$ is taken together with $R^2$ to form a 5- or 6-membered ring which is optionally substituted with one or more of the same or different $R^a$ or suitable $R^b$ groups;

$R^{3''}$ is selected from (C4-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^{3''}$ is taken together with $R^4$ to form a 5- or 6-membered ring which is optionally substituted with one or more of the same or different $R^a$ or suitable $R^b$ groups;

$R^4$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively $R^4$ is taken together with $R^{3''}$ to form a 5- or 6-membered ring which is optionally substituted with one or more of the same or different $R^a$ or suitable $R^b$ groups;

$R^5$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ group or, alternatively $R^5$ is taken together with $R^{6''}$ to form a 5- or 6-membered ring which is optionally substituted with one or more of the same or different $R^a$ or suitable $R^b$ groups;

$R^{6''}$ is selected from (C4-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups or, alternatively $R^{6''}$ is taken together with $R^5$ to form a 5- or 6-membered ring which is optionally substituted with one or more of the same or different $R^a$ or suitable $R^b$ groups;

$R^{6'}$ is selected from hydrogen, (C4-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively, $R^{6'}$ is taken together with $R^7$ to form a 5- or 6-membered ring optionally substituted with one or more of the same or different $R^a$ or suitable $R^b$ groups;

$R^7$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or $R^b$ groups, or, alternatively, $R^7$ is taken together with $R^{6'}$ to form a 5- or 6-membered ring optionally substituted with one or more of the same or different $R^a$ or suitable $R^b$ groups, or, alternatively, $R^7$ is taken together with $R^8$ to form part of a benzo, naptho or polycyclic aryleno group which is optionally substituted with one or more of the same or different $R^a$ or suitable $R^b$ groups;

$R^8$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^8$ together with $R^7$ form part of a benzo, naptho or polycyclic aryleno group which is optionally substituted with one or more of the same or different $R^a$ or suitable $R^b$ groups;

$R^{11}$ and $R^{15}$ are each, independently of one another, selected from hydrogen, halo, (C1-C20) alkyl, haloalkyl, —$OR^y$, —$SR^y$, —$SOR^y$, —$SO_2R^y$, —$C(O)OR^y$, —$S(O)_2OR^y$, amide, sulfonamide and nitrile;

$R^{12}$, $R^{13}$ and $R^{14}$ are each, independently of one another, selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups;

$R^x$ is selected from —$NR^cR^c$, —$OR^d$, —$SR^d$, halo, haloalkyl, —CN, —NC, —OCN, —SCN, —NO, —$NO_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$OC(O)R^d$, —$OC(O)OR^d$, —$OC(O)NR^cR^c$ and —$OC(NH)NR^cR^c$;

$R^y$ is selected from (C1-C20) alkyls or heteroalkyls optionally substituted with lipophilic substituents, (C5-C20) aryls or heteroaryls optionally substituted with lipophilic substituents and (C6-C26) arylalkyl or heteroarylalkyls optionally substituted with lipophilic substituents;

$R^a$ is selected from hydrogen, (C1-C8) alkyl or heteroalkyl, (C5-C20) aryl or heteroaryl and (C6-C28) arylalkyl or heteroarylalkyl;

$R^b$ is selected from —$NR^cR^c$, =O, —$OR^d$, =S, —$SR^d$, =$NR^d$, =$NOR^d$, halo, haloalkyl, —CN, —NC, —OCN, —SCN, —NO, —$NO_2$, =$N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$OC(O)R^d$, —$OC(O)OR^d$, —$OC(O)NR^cR^c$ and —$OC(NH)NR^cR^c$;

each $R^c$ is independently hydrogen or $R^d$, or, alternatively, each $R^c$ is taken together with the nitrogen atom to which it is bonded to form a 5 to 8-membered saturated or unsaturated ring which may optionally include one or more of the same or different additional heteroatoms and which may optionally be substituted with one or more of the same or different $R^a$ or $R^d$ groups;

each $R^d$ is independently $R^a$ or $R^a$ substituted with one or more of the same or different $R^a$ or $R^e$ groups;

each $R^e$ is selected from —$NR^aR^a$, =O, —$OR^a$, =S, —$SR^a$, =$NR^a$, =$NOR^a$, halo, haloalkyl, —CN, —NC, —OCN, —SCN, —NO, —$NO_2$, =$N_2$, —$N_3$, —$S(O)R^a$, —$S(O)_2R^a$, —$S(O)_2OR^a$, —$S(O)NR^aR^a$, —$S(O)_2NR^aR^a$, —$OS(O)R^a$, —$OS(O)_2R^a$, —$OS(O)_2OR^a$, —$OS(O)_2NR^aR^a$, —$C(O)R^a$, —$C(O)OR^a$, —$C(O)NR^aR^a$, —$C(NH)NR^aR^a$, —$OC(O)R^a$, —$OC(O)OR^a$, —$OC(O)NR^aR^a$ and —$OC(NH)NR^aR^a$.

In another embodiment, the lipid soluble rhodamine dyes comprising core structure (I) are as described in U.S. Pat. Nos. 5,231,191, 5,366,860, 5,410,053, 5,750,409, 5,840,999, 5,847,162, 5,936,087, 6,008,379 and 6,248,884 with the exception that at least one, and as many as all, of $R^{3'}$, $R^{3''}$, $R^{6'}$ and $R^{6''}$ are selected from lipophilic moieties. Accordingly, these patents are hereby incorporated by reference. Once again, non-limiting examples of lipophilic moieties include (C4-C20) alkyls, (C5-C20) aryls, and (C6-C40) arylalkyls.

In another embodiment, the lipid soluble rhodamine dyes comprise core structure (I) and, additionally, the substituents therein comprise one or more of the following features: $R^1$ and $R^8$ are each, independently of one another, selected from hydrogen, (C1-C8) alkyl, halo, and —$CF_3$, or are part of a fused aryl or heteroaryl group with $R^2$ and $R^7$, respectively; $R^2$ and $R^7$ are each, independently of one another, selected from hydrogen, (C1-C8) alkyl, halo, —$CF_3$, —CN, carboxylate, ester, sulfone, amino, amido and oxoether, or are part of a fused aryl or heteroaryl group with $R^1$ and $R^8$, respectively, or are part of a 5 or 6 membered ring with $R^{3'}$ and $R^{6'}$, respectively; $R^{3'}$ and $R^{6'}$ are each, independently of one another, selected from hydrogen and (C4-C20) alkyl, or are part of a 5 or 6 membered ring with $R^2$ and $R^7$, respectively; $R^{3''}$ and $R^{6''}$ are each, independently of one another, selected from hydrogen and (C4-C20) alkyl or are part of a 5 or 6 membered ring with $R^4$ and $R^5$, respectively; at least two of $R^{3'}$, $R^{3''}$, $R^{6'}$, $R^{6''}$ are not hydrogen; $R^4$ and $R^5$ are each, independently of one another, selected from hydrogen, (C1-C8) alkyl, halo, —$CF_3$, aryl, heteroaryl, —CN, carboxylate, ester, and sulfone, or are part of a 5 or 6 membered ring with $R^{3''}$ and $R^{6''}$, respectively; $R^{11}$ and $R^{15}$ are each, independently, selected from hydrogen, halo, ester, amide, sulfonamide, (C1-C20) alkyl, —$OR^e$, —$SR^e$, —CN and sulfone; and $R^{12}$, $R^{13}$ and $R^{14}$ are each, independently of one another, selected from hydrogen, halo, alkyl, aryl, (C4 to C20) alkyl ester, sulfone, —$CF_3$ and —CN.

In yet another embodiment, the lipid soluble rhodamine dyes comprise core structure (I) and, additionally, the substituents therein comprise one or more of the following features: $R^1$ and $R^8$ are each, independently of one another, selected from hydrogen, (C1-C8) alkyl, and halo, or are part of a fused aryl or heteroaryl group with $R^2$ and $R^8$, respectively; $R^2$ and $R^7$ are each, independently of one another, selected from hydrogen, (C1-C8) alkyl, and halo, or are part of a fused aryl or heteroaryl group with $R^1$ and $R^8$ respectively, or are part of a 5 or 6 membered ring with $R^{3'}$ and $R^{6'}$, respectively; $R^{3'}$ and $R^{6'}$ are each the same or different (C4-C20) alkyl; $R^{3''}$ and $R^{6''}$ are each, independently of one another, selected from hydrogen and the same or different (C4-C20) alkyl, or are part of a 5 or 6 membered ring with $R^4$ and $R^5$, respectively; $R^4$ and $R^5$ are each, independently of one another, selected from hydrogen, (C1-C8) alkyl, aryl and heteroaryl and halo, or are part of a 5 or 6 membered ring with $R^{3''}$ and $R^{6''}$, respectively; $R^{11}$ and $R^{15}$, independently of one another, selected from hydrogen, fluoro, chloro, (C1-C20) alkyl, —$OR^e$ and —$SR^e$; and $R^{12}$, $R^{13}$ and $R^{14}$ are each, independently of one another, selected from hydrogen and halo.

In still another embodiment, the lipid soluble rhodamine dyes comprise one of the following structural embodiments of core structure (I):

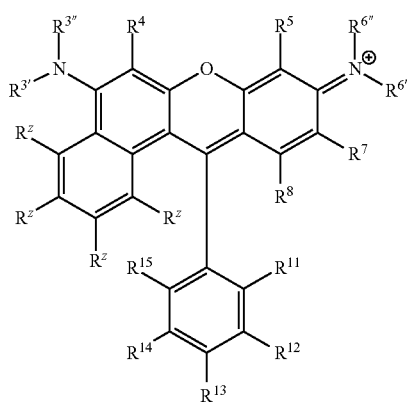
(Ia)
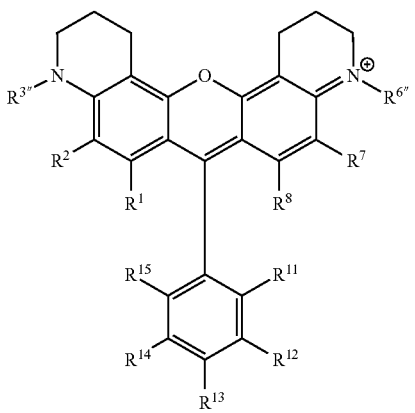
(Ib)
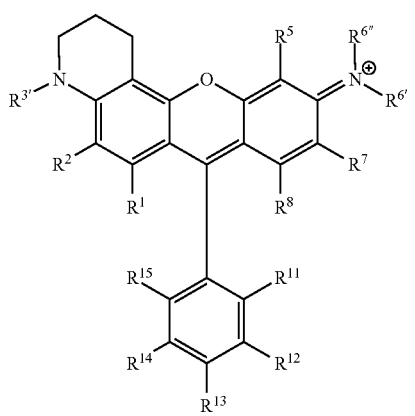
(Ic)
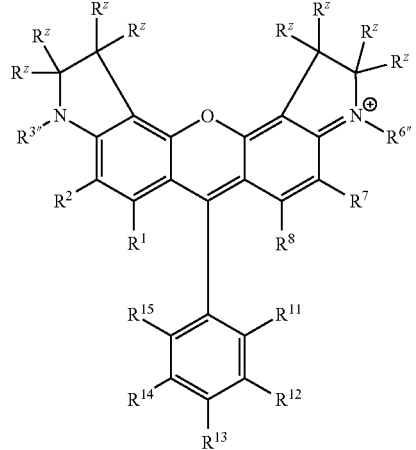
(Id)
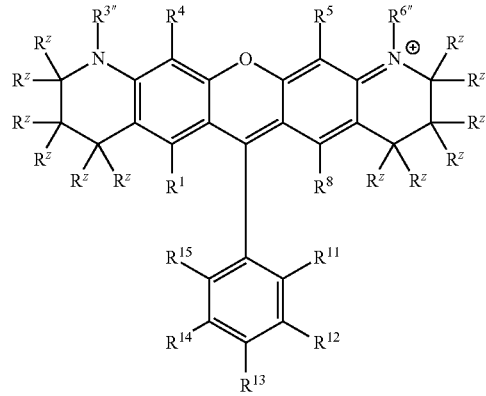
(Ie)
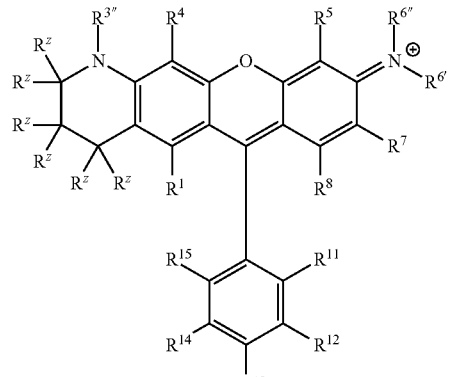
(If)
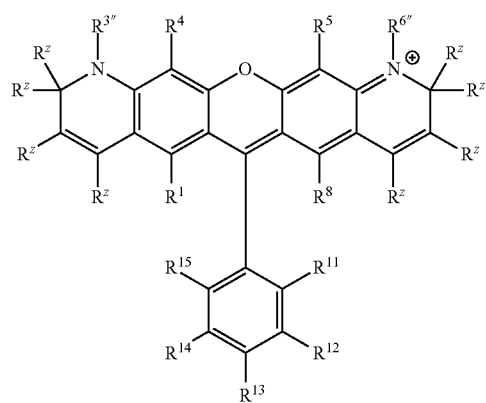
(Ig)

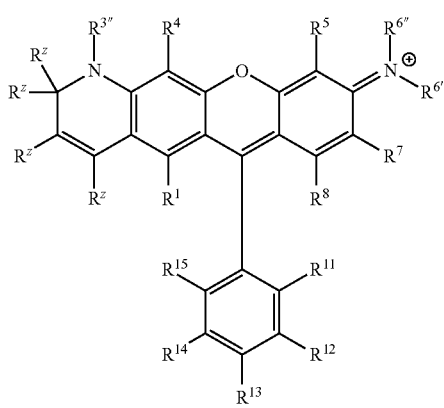

(Ih)

(Ii)

(Ij)

wherein each $R^z$ is independently selected from hydrogen, $R^b$, (C1-C20) alkyl optionally substituted with one or more of the same or different $R^b$ groups, (C5-C20) aryl optionally substituted with one or more of the same or different $R^a$ or suitable $R^b$ groups and (C6-C40) arylalkyl optionally substituted with one or more of the same or different $R^a$ or suitable $R^b$ group; and $R^1$, $R^2$, $R^{3'}$, $R^{3''}$, $R^4$, $R^5$, $R^{6''}$, $R^6$, $R^7$, $R^8$, $R^{11}$, $R^{12}$, $R^{13}$, $R^{14}$, $R^{15}$, $R^a$ and $R^b$ are as previously defined. Often, $R^z$ is selected from hydrogen and (C1-C8) alkyl.

The following lipid soluble rhodamine dyes are non-limiting examples of dyes that comprise core structure (I):

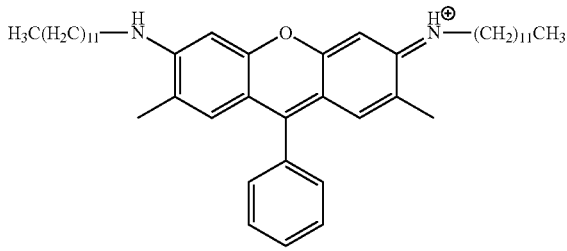

Dye (1)

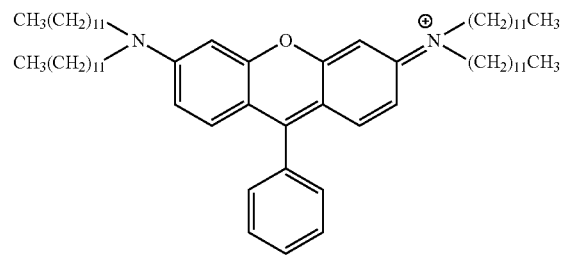

Dye (2)

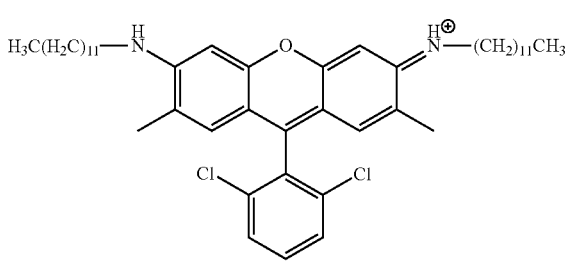

Dye (3)

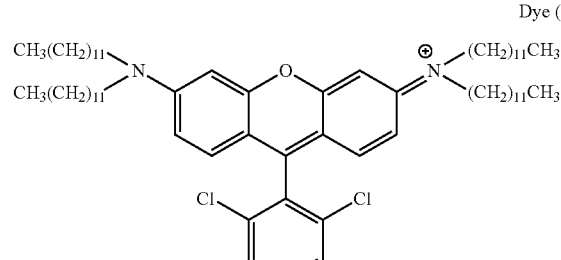

Dye (4)

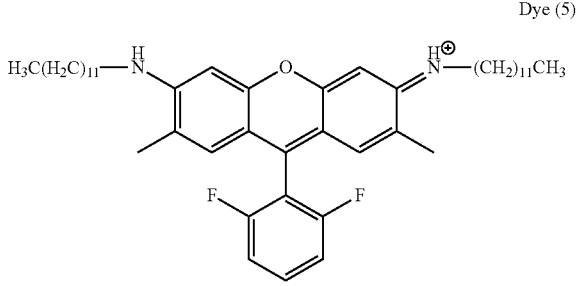

Dye (5)

Dye (6)
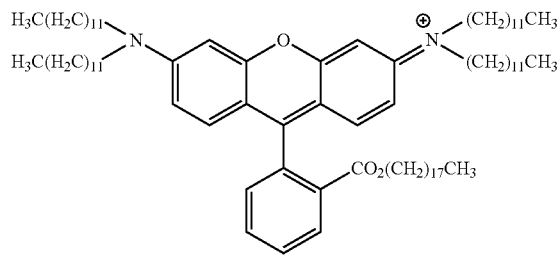

Dye (7)
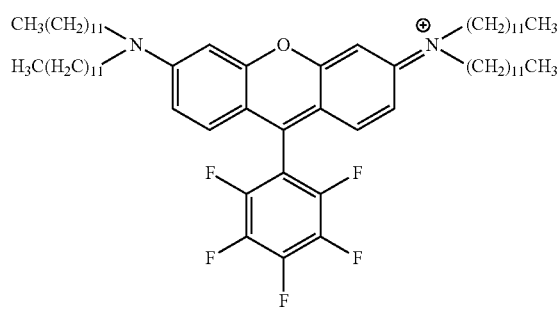

Dye (8)
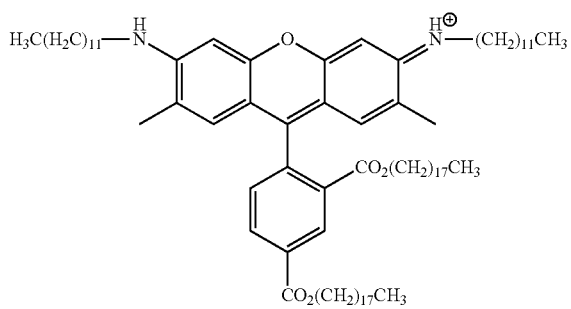

Dye (9)
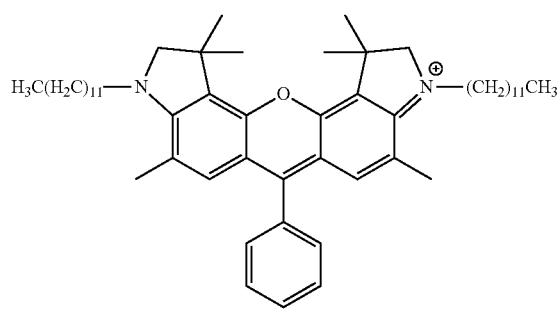

Dye (10)
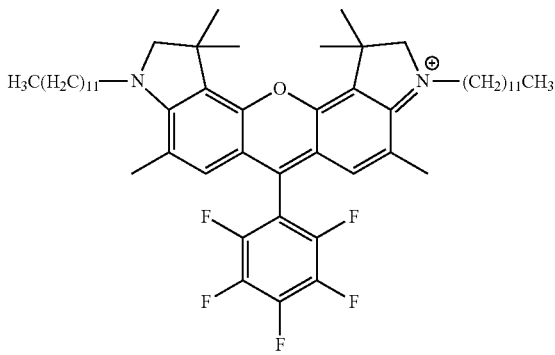

5.7 Structure (II) Dyes

In one embodiment, the lipid soluble rhodamine dyes comprise core structure (II) and, additionally, the substituents therein are defined as follows:

$R^1, R^2, R^{3'}, R^{3''}, R^4, R^5, R^{6''}, R^{6'}, R^7, R^8, R^x, R^a, R^b, R^c, R^d$, and $R^e$ are as first defined in section 5.6 with respect to core structure (I); and $R^9$ is selected from hydrogen, alkyl, halo, haloalkyl, or nitrile.

In another embodiment, extended rhodamines comprising core structure (II) are as described in U.S. Pat. Nos. 6,008,379 and 5,936,087, with the exception that at least one, and as many as all, of $R^{3'}, R^{3''}, R^{6'}$ and $R^{6''}$ are selected from lipophilic moieties. Accordingly, these patents are hereby incorporated by reference. Furthermore, these rhodamines can be extended as previously discussed and illustrated in U.S. Pat. No. 6,248,884, which is also incorporated herein by reference. Non-limiting examples of lipophilic moieties include (C4-C20) alkyls, (C5-C20) aryls and (C6-C40) arylalkyls.

In another embodiment, the lipid soluble rhodamine dyes comprise core structure (II) and the substituents therein comprise one or more of the following features: $R^1$ when taken together with $R^2$ forms part of a fused benzo, naptho or polycyclic aryleno group that is optionally substituted with one or more of the same or different $R^a$ or suitable $R^b$ groups; $R^7$ when taken together with $R^8$ form part of a fused benzo, naptho or polycyclic aryleno group that is optionally substituted with one or more of the same or different $R^a$ or suitable $R^b$ groups; and $R^9$ is hydrogen.

In yet another embodiment, the lipid soluble rhodamine dyes comprise one of the following structural embodiments of core structure (II):

(IIa)
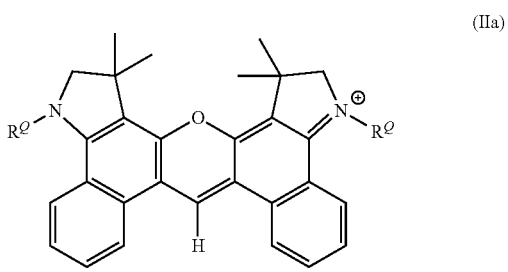

(IIb)
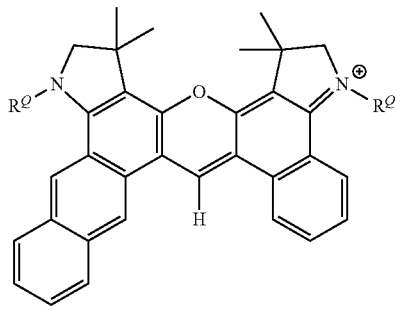

(IIc)
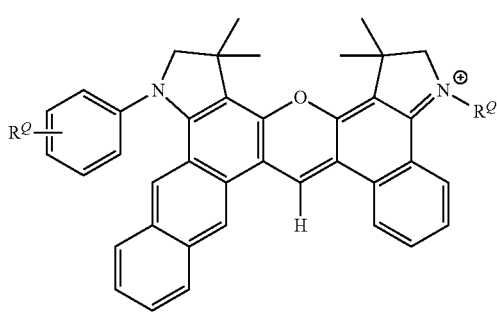

(IId)
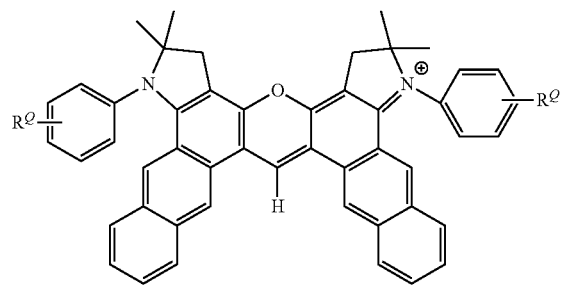

wherein each $R^Q$ is independently selected from hydrogen, (C1-C20) alkyl optionally substituted with one or more of the same or different $R^b$ groups, (C5-C20) aryl optionally substituted with one or more of the same or different $R^a$ or suitable $R^b$ groups and (C6-C40) arylalkyl optionally substituted with one or more of the same or different $R^a$ or suitable $R^b$ group; and $R^a$ and $R^b$ are as previously defined. Preferably, each $R^Q$ is independently selected from the group consisting of hydrogen and (C1-C8) alkyl.

The following lipid soluble rhodamine dyes are non-limiting examples of specific dyes that comprise core structure (II):

Dye (11)
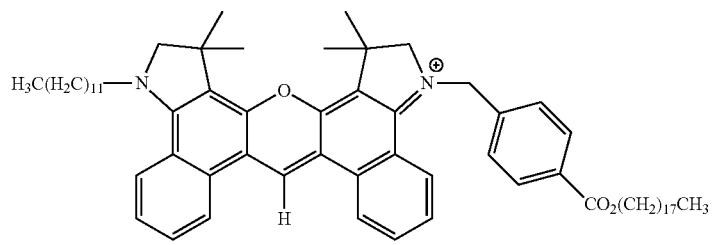

Dye (12)
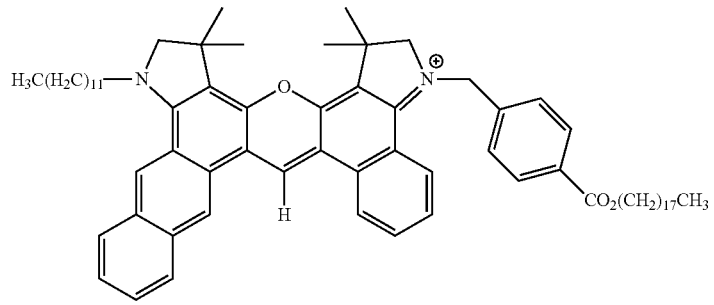

Dye (13)
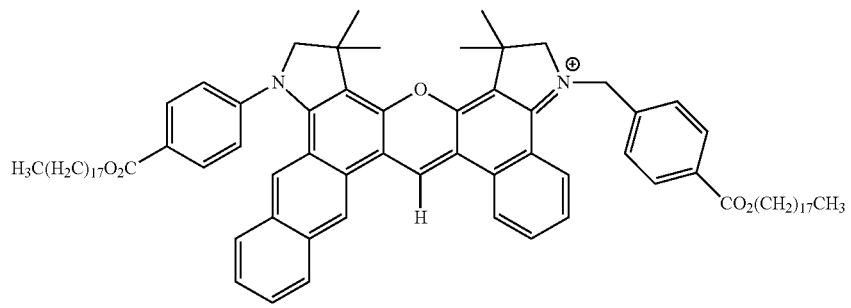

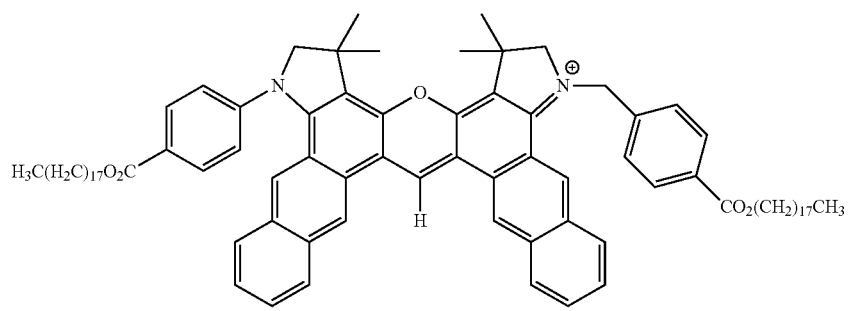

Dye (14)

5.8 Structure (III) Dyes

In one embodiment, the lipid soluble rhodamine dyes comprise core structure (III) and, additionally, the substituents therein are defined as follows:

$R^1, R^{3'''}, R^5, R^{6'''}, R^{6'}, R^7, R^8, R^{11}, R^{12}, R^{13}, R^{14}, R^{15}$ $R^x, R^y$, $R^a, R^b, R^c, R^d$, and $R^e$ are as first defined in section 5.6 with respect to core structure (I);

$R^2$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^2$ is taken together with $R^1$ or $R^{2'}$ to form part of a benzo, naptho or polycyclic aryleno group which is optionally substituted with one or more of the same or different $R^a$ or suitable $R^b$ groups;

$R^{2'}$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or suitable $R^b$ groups, or, alternatively, $R^{2'}$ is taken together with $R^2$ to form part of a benzo, naptho or polycyclic aryleno group which is optionally substituted with one or more of the same or different $R^a$ or suitable $R^b$ groups, or, alternatively, $R^{2'}$ is taken together with $R^{3'}$ to form a 5- or 6-membered ring which is optionally substituted with one or more of the same or different $R^a$ or suitable $R^b$ groups;

$R^{3'}$ is selected from hydrogen, (C4-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively, $R^{3'}$ is taken together with $R^{2'}$ to form a 5- or 6-membered ring which is optionally substituted with one or more of the same or different $R^a$ or suitable $R^b$ groups;

$R^4$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively $R^4$ is taken together with $R^{3'''}$ to form a 5- or 6-membered ring which is optionally substituted with one or more of the same or different $R^a$ or suitable $R^b$ groups, or, alternatively, $R^4$ is taken together with $R^{4'}$ to form part of a benzo, naptho or polycyclic aryleno group which is optionally substituted with one or more of the same or different $R^a$ or suitable $R^b$ groups; and $R^{4'}$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively $R^{4'}$ is taken together $R^4$ to form part of a benzo, naptho or polycyclic aryleno group which is optionally substituted with one or more of the same or different $R^a$ or suitable $R^b$ groups.

In another embodiment, extended rhodamines comprising core structure (III) are as described in U.S. Pat. No. 6,248,884 with the exception that at least one, and as many as all, of $R^{3'}$, $R^{3'''}$, $R^{6'}$ and $R^{6'''}$ are selected from lipophilic moieties. Accordingly, U.S. Pat. No. 6,248,884 is hereby incorporated by reference. Non-limiting examples of lipophilic moieties include (C4-C20) alkyls, (C5-C20) aryls, and (C6-C40) arylalkyls.

In yet another embodiment, the extended rhodamines comprising core structure (III) additionally comprises one or more substituted or unsubstituted five or six membered fused rings that comprise, as part of the ring, a nitrogen atom from either the exocyclic amine or exocyclic imminium group and one of $R^{2'}$, $R^4$, $R^5$ or $R^7$. For example, $R^{2'}$ can form a fused substituted or unsubstituted five or six membered ring with $R^{3'}$. Alternatively, $R^4$ can form a fused substituted or unsubstituted five or six membered ring with $R^{3'''}$. Alternatively, $R^5$ can form a fused substituted or unsubstituted ring with $R^{6'''}$. Alternatively, $R^7$ can form a fused substituted or unsubstituted ring with $R^{6'}$. Often two fused rings are present, one that includes the imminium nitrogen and one that includes the amine nitrogen. Illustrative substituent groups on the five or six membered rings include $R^a$ or suitable $R^b$ groups. In one embodiment the substituents on the five or six membered rings include (C7-C20) alkyls, phenyl or alkylphenyl groups, and (C7-C20) alkylester substituted phenyl or alkylphenyl groups.

5.9 Structure (IV) Dyes

In one embodiment, the lipid soluble rhodamine dyes comprise core structure (IV) and, additionally, the substituents therein are defined as follows:

$R^1, R^{3'''}, R^{6'''}, R^8, R^{11}, R^{12}, R^{13}, R^{14}, R^{15}, R^x, R^y, R^a, R^b, R^c, R^d$, and $R^e$ are as first defined in section 5.6 with respect to core structure (I);

$R^2$, $R^{2'}$, $R^{3'}$, $R^4$, and $R^{4'}$ are as defined in section 5.8 with respect to core structure (III);

$R^{5'}$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ group or, alternatively $R^5$ is taken together with $R^5$ to form part of a benzo, naptho or polycyclic aryleno group which is optionally substituted with one or more of the same or different $R^a$ or suitable $R^b$ groups.

$R^5$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ group or, alternatively $R^5$ is taken together with $R^{6'}$ to form a 5- or 6-membered ring which is optionally substituted with one or more of the same or different $R^a$ or suitable $R^b$ groups, or, alternatively, $R^5$ is taken together with $R^{5'}$ to form part of a benzo, naptho or polycyclic aryleno group which is optionally substituted with one or more of the same or different $R^a$ or suitable $R^b$ groups;

$R^{6'}$ is selected from hydrogen, (C4-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroarylalkyl optionally substituted with one or more of the same or different $R^a$ or suitable $R^b$ groups, or, alternatively, $R^{6'}$ is taken together with $R^{7'}$ to form a 5- or 6-membered ring optionally substituted with one or more of the same or different $R^a$ or suitable $R^b$ groups;

$R^{7'}$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or $R^b$ groups, or, alternatively, $R^{7'}$ is taken together with $R^{6'}$ to form a 5- or 6-membered ring optionally substituted with one or more of the same or different $R^a$ or suitable $R^b$ groups, or, alternatively, $R^{7'}$ is taken together with $R^7$ to form part of a benzo, naptho or polycyclic aryleno group which is optionally substituted with one or more of the same or different $R^a$ or suitable $R^b$ groups; and $R^7$ is selected from hydrogen, $R^x$, (C1-C20) alkyl or heteroalkyl optionally substituted with one or more of the same or different $R^b$ groups, (C5-C20) aryl or heteroaryl optionally substituted with one or more of the same or different $R^a$ or suitable $R^b$ groups and (C6-C40) arylalkyl or heteroaryl alkyl optionally substituted with one or more of the same or different $R^a$ or $R^b$ groups, or, alternatively, $R^7$ is taken together with $R^{7'}$ or $R^8$ to form part of a benzo, naptho or polycyclic aryleno group which is optionally substituted with one or more of the same or different $R^a$ or suitable $R^b$ groups.

In another embodiment, extended rhodamines corresponding to core structure (IV) are as described in U.S. Pat. No. 6,248,884 with the exception that at least one, and as many as all, of $R^{3'}$, $R^{3''}$, $R^{6'}$ and $R^{6''}$ are selected from lipophilic moieties. Accordingly, U.S. Pat. No. 6,248,884 is hereby incorporated by reference. Non-limiting examples of lipophilic moieties include (C4-C20) alkyls, (C5-C20) aryls, and (C6-C40) arylalkyls.

In yet another embodiment, the extended rhodamines comprising core structure (IV) additionally comprises one or more substituted or unsubstituted five or six membered fused rings that comprise, as part of the ring, a nitrogen atom from either the exocyclic amine or exocyclic imminium group and one of $R^{2'}$, $R^4$, $R^5$ or $R^7$. For example, $R^{2'}$ can form a fused substituted or unsubstituted five or six membered ring with $R^{3'}$. Alternatively, $R^4$ can form a fused substituted or unsubstituted five or six membered ring with $R^{3''}$. Alternatively, $R^5$ can form a fused substituted or unsubstituted ring with $R^{6''}$. Alternatively, $R^{7'}$ can form a fused substituted or unsubstituted ring with $R^{6'}$. Often two fused rings are present, one that includes the imminium nitrogen and one that includes the amine nitrogen. Illustrative substituent groups on the five or six membered rings include $R^a$ or suitable $R^b$ groups. In one embodiment the substituents on the five or six membered rings include (C7-C20) alkyls, phenyl or alkylphenyl groups, and (C7-C20) alkylester substituted phenyl or alkylphenyl groups.

5.10 Linking Groups

As discussed previously, in some embodiments, the lipid-soluble rhodamine dye may be attached to the polymeric material by way of a covalent linkage. In such embodiments, the lipid-soluble rhodamine dye will typically include a linking group suitable for forming the covalent linkage. The identity of the linking group will depend upon the functional group of the polymer to which the lipid-soluble rhodamine dye will be attached, and will be apparent to those of skill in the art. In one embodiment, the linking group is a nucleophilic or electrophilic group capable of forming a covalent linkage with a complementary electrophilic or nucleophilic group on the polymer. Non-limiting examples of suitable electrophilic linking groups include any one or a combination of the following: amines/anilines, alcohols/phenols, thiols, hydrazines and hydroxylamines. Non-limiting examples of suitable electrophilic linking groups include any one or a combination of the following: activated esters such as pentafluorophenyl ester and NHS-ester, acrylamides, acyl azides, acyl halides, acyl nitriles, aldehydes or ketones, alkyl halides, alkyl sulfonates, anhydrides, aryl halides, aziridines, boronates, carboxylic acids, carbodiimides, diazoalkenes, epoxides, haloacetamides, halotriazines, imido esters, isocyanates, isothiocyanates, maleimides, phosphoramidites, silyl halides, sulfonate esters and sulfonyl halides.

The linking group may be attached directly to the lipid-soluble rhodamine or it may be spaced away from the rhodamine by way of a spacing moiety. The nature of the spacing moiety is not critical, and may vary broadly. For example, the spacing moiety may be a substituted or unsubstituted alkylene or heteroalkylene, a substituted or unsubstituted arylene or heteroarylene, a substituted or unsubstituted arylalkylene or heteroarylalkylene, or a combination of such groups. In one embodiment, the spacing moiety is an unsubstituted alkylene of the formula $-(CH_2)_n-$, where n is an integer ranging from 1 to 40, typically from 1 to 20 and more typically from 1 to 10. Other exemplary spacing moieties suitable for spacing the linking group from the remainder of the lipid-soluble rhodamine molecule are described, for example, in U.S. Pat. Nos. 5,863,727, 5,847,162, 6,229,055, 6,248,884, and 6,372,907. A lipid-soluble rhodamine may include one or a plurality of linking groups, which may be the same or different.

In one embodiment, a lipid-soluble rhodamine suitable for covalent attachment to the polymer is any of the previously-described lipid-soluble rhodamines in which one or $R^1$, $R^2$, $R^{2'}$, $R^4$, $R^{4'}$, $R^5$, $R^{5'}$, $R^7$, $R^{7'}$, $R^8$, $R^{11}$, $R^{12}$, $R^{13}$, $R^{14}$ or $R^{15}$ is a substitutent of the formula —S-LG, where S represents a bond or a spacing moiety and LG represents a linking group. In a specific embodiment, one of $R^4$, $R^5$, $R^{12}$, $R^{13}$ or $R^{14}$ is —S-LG.

5.11 Energy Transfer Dyes

The lipid soluble rhodamine dyes may be part of an energy transfer ("ET") network comprising, for example, two to four dyes covalently attached to one another that transfer energy to generate a longer Stoke's shift. One example of an ET network would be a fluorescence resonance energy transfer ("FRET") dye. In other words, the lipid soluble rhodamine dyes may be part of series of dyes that are covalently attached to one another wherein at least one of the dyes is a lipid soluble rhodamine. Linkages for covalently attaching rhodamine dyes to other dyes are known in the art, as are suitable locations for attachment to the rhodamine dyes (see, e.g., U.S. Pat. Nos. 5,800,996 and 5,863,727). In one embodiment, each dye in the energy transfer network is within 5 to 100 Å of the neighboring dye or dyes in the network to which it is covalently attached. In such embodiments, the lipid soluble rhodamine dye can be the donor, acceptor, or an intermediate dye in the network.

Thus, in one embodiment, the lipid-soluble rhodamine dyes useful in the fluorescent polymeric materials of the invention include any lipid-soluble dye comprising one of the following "core" structures:

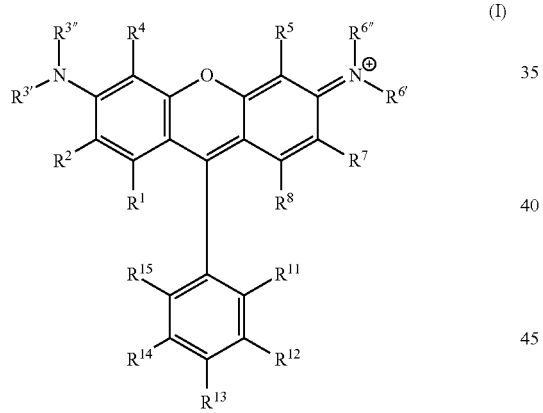

(I)

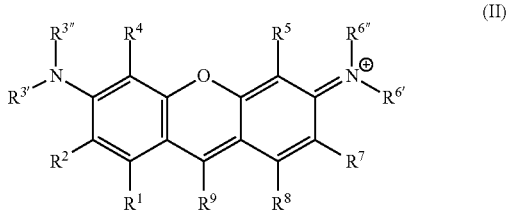

(II)

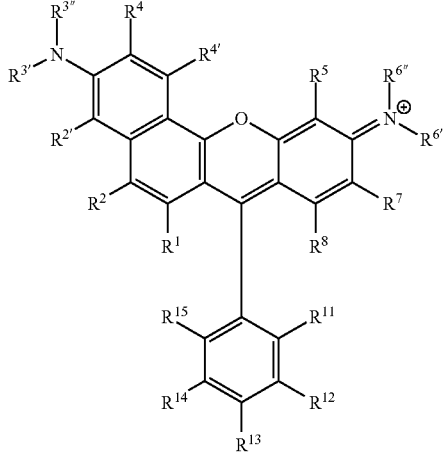

(III)

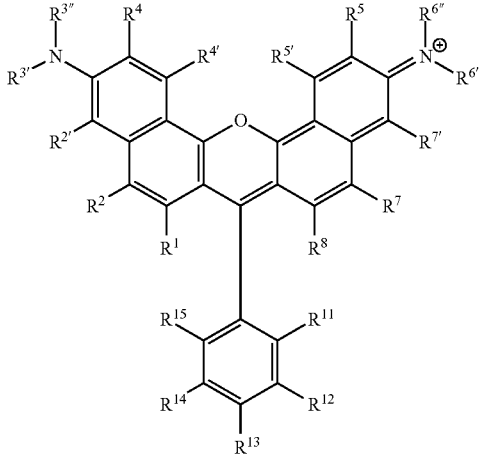

(IV)

wherein where at least one of $R^{3'}$, $R^{3''}$, $R^{6''}$ and $R^{6'}$ represents a lipophilic substituent, $R^9$ (present in core structure (II) only) is a nonaromatic substituent, at least one of $R^2$, $R^{2'}$, $R^{3'}$, $R^4$, $R^{4'}$, $R^{5'}$, $R^5$, $R^{6'}$, $R^{7'}$, $R^7$, $R^{12}$, $R^{13}$, and $R^{14}$ corresponds to the moiety —$S^1$-LK-$S^2$-D, and the remainder of $R^1$, $R^2$, $R^{2'}$, $R^{3'}$, $R^{3''}$, $R^4$, $R^{4'}$, $R^{5'}$, $R^5$, $R^{6'}$, $R^{6''}$, $R^{7'}$, $R^7$, $R^8$, $R^9$, $R^{11}$, $R^{12}$, $R^{13}$, $R^{14}$ and $R^{15}$ are, independently, selected from hydrogen or the same or different substituent groups having no more than 40 atoms. In this instance, D represents a covalently attached acceptor or donor dye and the moieties $S^1$, LK, and $S^2$ form what is known in the art as a "linker"—which embraces any functionality known in the art that attaches one dye to another.

The identity of donor or acceptor dye D is not critical, so long as it can donate or accept energy from or to the particular lipid-soluble rhodamine to which it is attached. Dyes that can act as donor or acceptors for rhodamines are well-known, and include, for example, fluoresceins, rhodamines, cyanines, phthalocyanine and squaraine dyes. Any of these dyes, or another lipid-soluble rhodamine as described herein, may be used as the donor dye or acceptor dye in an energy transfer dye comprising a lipid-soluble rhodamine. The ability to select a suitable dye D for a particular lipid-soluble rhodamine is within the routine skill in the art.

$S^1$ and $S^2$ are, independently of one another, a covalent bond or a spacing moiety Like the previously-described spacing moiety "S," the nature of spacing moieties $S^1$ and $S^2$ may vary broadly, and may include substituted or unsubstituted alkylene or heteroalkylenes, substituted or unsubstituted arylenes or heteroarylene, or substituted or unsubstituted arylalkylenes or heteroarylalkylenes, or combinations thereof.

LK represents a linkage, which may be a bond or another type of linkage, such as a linkage formed between a nucleophilic (or electrophilic) group and a complementary electrophilic (or nucleophilic) group. In one embodiment, LK is selected from an ester, an amide, a sulfonamide, a hydrazine, an imine, a maleimide, a sulfide, a disulfide, a carbamate and a thiocarbamate linkage.

As will be appreciated by skilled artisans, the various substitutents $S^1$, LK and S of the linker should be selected to position the lipid-soluble rhodamine and acceptor or donor dye in close enough proximity to one another such that the dyes can undergo energy transfer, whether via FRET or another mechanism.

Suitable linkers are illustrated, for example, by U.S. Pat. Nos. 5,800,996 and 5,863,727, issued to Lee et al., U.S. Pat. No. 6,008,279, issued to Benson et al., and U.S. Pat. No. 5,654,419, issued to Mathies et al., all of which are hereby incorporated by reference. Methods of synthesizing such energy transfer dyes, as well as suitable points of attachment for covalently coupling the lipid-soluble rhodamine and acceptor or donor dye D to one another are also described in these patents.

In one exemplary embodiment, an energy transfer dye of the formula $D^1$-$S^1$-LK-$S^2$-D, where $D^1$ represents a lipid-soluble rhodamine dye and $S^1$, LK, $S^2$ and D are as defined above may be synthesized by reacting a lipid-soluble rhodamine dye of the formula $D^1$-$S^1$-LG, where LG represents a linking group, with a donor or acceptor dye of the formula D-$S^2$-LG', where LG' represents a linking group which is complementary to linking group LG such that LG and LG' may react with one another to form linkage LK. As a specific embodiment, LG may be an activated ester such as an NHS-ester and LG' may be a primary amino group, such that reaction forms an amide linkage LK.

5.12 Dye Combinations

The lipid soluble rhodamine dyes may be used in combination with one another. The lipid soluble rhodamine dyes may also be used in combination with any other class of dye that is fluorescent and can be attached and/or absorbed into the polymer. In one embodiment, a combination of dyes is employed wherein all of the dyes fluoresce when irradiated by the same excitation source. In another embodiment, multiple excitation sources are employed.

Nonlimiting examples of additional dyes that may be employed include acridine dyes, alizarene dyes, azo dyes, anthraquinine dyes, bodipy dyes, coumarin dyes, cyanine dyes, fluorescein dyes such as AMFAM and PET, lanthanide complexes, oxazine dyes, phenazathionium dyes, phenazoxonium dyes, porphyorin dyes, pyrene dyes, pyrilium dyes, perylene dyes, phenoxazine dyes, phenezine dyes, rhodol dyes and xanthene dyes. Other dyes that may be utilized include, but are not limited to the following: squaraine derivatives; phthalocyanines; naphthalocyanines, 3-Hydroxypyrene 5,8,10-Tri Sulfonic acid, 5-Hydroxy ryptamine, 5-Hydroxy Tryptamine (5-HT), Acid Fuhsin, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocoumarin, Anthroyl Stearate, Aryl- or Heteroaryl-substituted Polyolefin, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy F1, BOPRO 1, Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, DAPI, Diamino Phenyl Oxydiazole (DAO), Dimethylamino-5-Sulphonic acid, Dipyrrometheneboron Difluoride, Diphenyl Brilliant Flavine 7GFF, Dopamine, Eosin, Erythrosin ITC, Ethidium Bromide, Euchrysin, FIF (Formaldehyde Induced Fluorescence), Flazo Orange, Fluo 3, Fluorescamine, Fura-2, Genacryl Brilliant Red B, Genacryl Brilliant Yellow 10 GF, Genacryl Pink 3G, Genacryl Yellow 5 GF, Gloxalic Acid, Granular Blue, Haematoporphyrin, Hoechst 33258, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nile Red, Nitrobenzoxadidole, Noradrenaline, Nuclear Fast Red, Nuclear Yellow, Nylosan Brilliant Flavin EBG, Oregon Green, Oxazine, Oxazole, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7 GF, Quinacrine Mustard, Rhodamine 123, Rhodamine 5 GLD, Rhodamine 6 G, Rhodamine B, Rhodamine B 200, Rhodamine B Extra, Rhodamine BB, Rhodamine BG, Rhodamine WT, Rose Bengal, Serotonin, Sevron Brilliant Red 2 B, Sevron Brilliant Red 4 G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Texas Red, Thiazine Red R, Thioflavin S, Thioflavin TCN, Thioflavin 5, hiolyte, Thiozol Orange, Tinopol CBS, TOTO 1, TOTO 3, True Blue, Ultralite, Uranine B, Uvitex SFC, Xylene Orange, XRITC, YO PRO1, or combinations thereof.

In one embodiment, a lipid soluble rhodamine dye is used in combination with a total of one to ten additional dyes which may include additional lipid soluble rhodamine dyes. When the dyes are not covalently attached to the polymer component, it is beneficial for the dyes to be soluble a common hydrophobic organic solvent to minimize the steps necessary to adequately imbibe the dyes into the polymer.

The fluorescent dyes are selected based on the desired emission, absorption and solubility properties. The spectral properties of the fluorescent dyes selected should be sufficiently close in excitation wavelengths and intensity to the lipid soluble rhodamine dyes to permit the use of the same analytical equipment, e.g., flow cytometry equipment.

5.13 Methods of Dye Synthesis

The lipid-soluble rhodamine dyes may be synthesized by well-known methods or by routine modification of such methods. For example, lipid-soluble rhodamine dyes which include a C9-phenyl substitutent having an ortho carboxylate or sulfonate substituent may be prepared by the methods described in U.S. Pat. Nos. 6,372,907, 6,248,884, 6,020,481, 6,008,379, 5,847,162, 5,936,087, 5,847,162, 5,750,409, 5,410,053 and 5,231,191, the disclosures of which are incorporated herein by reference. Lipid-soluble rhodamine dyes which include an "extended rhodamine" parent ring, as exemplified by structures (III) and (IV) may be prepared by the methods described in U.S. Pat. Nos. 6,248,884 and 6,008,379, the disclosures of which are incorporated herein by reference. Lipid-soluble rhodamine dyes which include a non-phenyl C9 substitutent, as exemplified by structure (II), may be prepared by the methods described in U.S. Pat. Nos. 5,936,087 and 6,248,884, the disclosures of which are incorporated herein by reference. Lipid-soluble rhodamine dyes which include a C9-phenyl substitute which does not have an ortho carboxylate or sulfonate substituent may be prepared by the methods illustrated in FIGS. 1, 2 and 3 as well as the methods described in copending patent application Ser. No. 10/837,621, now U.S. Pat. No. 7,491,830, entitled "Phenyl Xanthene Dyes," filed concurrently herewith, the disclosurse of which is incorporated herein by reference. Additional methods are provided in the Examples section.

5.14 Methods of Dye Incorporation

The method of incorporating the dye or dye mixture into or onto the polymer depends on a number of factors, including the desired characteristics of the fluorescent polymeric material, the intended method and environment for using the fluorescent polymeric material, economic considerations, availability of certain items, etc. The fluorescent dyes can be incorporated into the polymer by any method known in the art including, without limitation: (i) suspending the dyes and polymer in miscible solvent; and (ii) adding polymer to an organic solvent that swells, but does not dissolve, the polymer, then adding dye in organic solvent, and then shrinking the dye filled polymers with a polar solvent such as methanol.

In one embodiment, the dyes are incorporated internally into polymer microparticles, typically without covalent attachment, by absorption of the dyes into the polymeric microparticles while the dyes are dissolved in an organic solvent. This offers the great advantage of being able to prepare uniform microparticles with desired properties by carefully optimized procedures prior to adding the fluorescent dye. This also permits more flexibility in adjusting the relative concentrations of the dyes. Furthermore, the dyes can be distributed throughout the particles at higher concentrations than practically attainable by covalent chemical attachment. Such methods are known in the art and generally described in U.S. Pat. No. 6,268,222 which is incorporated herein by reference.

For example, the lipid soluble rhodamine dyes, being freely soluble in organic solvents, such as ethyl acetate and dichloromethane, and sparingly soluble in water, are easily introduced by solvent-based addition of the dyes to previously manufactured polymeric material. Other suitable solvents for this purpose include aromatic hydrocarbons, such as benzene, toluene, xylene; chlorinated hydrocarbons such as chloroform and methylene chloride (preferably mixed with an alcohol like methanol at about 30% so that the beads do not dissolve); pyridine; ethers like dioxane; tetrahydrofuran; esters such as n-butylphthalate, ethyl phthalate, butylacetate; hydrocarbons such as cyclohexane, methyl cyclohexane, ethylcyclohexane; carbon disulfide; and nitropropane.

For example, a quantity of microparticles can be soaked in a $1 \times 10^{-4}$ to $5 \times 10^{-3}$ molar solution of dye in ethyl acetate. The concentration employed is not critical as long as it is sufficient to imbibe enough of the dye into the microparticles for the microparticles to fluoresce. Similarly, the amount of microparticles employed is not critical as long as the microparticles are fully immersed in the solution so that they can absorb the dye. The microparticles are kept in contact with the solution for a time sufficient for the microparticles to swell and, thereby, absorb the dyes. Generally, one hour is sufficient. Once the microparticles have swollen and a sufficient quantity of the dyes has been absorbed, the microparticles are be made to shrink, thereby entrapping the dyes. Shrinking can be done in a number of ways. For hydrophobic polymers such as polystyrene, shrinking is easily accomplished by adding a large quantity (e.g., 5 fold by volume) of alcoholic solvent to the solution. An illustrative alcoholic solvent for this purpose is isopropanol. The microparticles are kept at room temperature for a time sufficient to insure shrinking. Generally, 30 minutes is sufficient. The microparticles are then separated from solution by centrifuge or any other known means of separation and subsequently washed with more alcoholic solvent.

Alternatively, it is often sufficient simply to admix the polymers and dyes in a mutual solvent. Preferred solvents include chlorinated aliphatic solvents such as dichloromethane, chloroform, and carbon tetrachloride. Alternative solvents include aromatic hydrocarbons such as benzene, toluene, and xylene. Other solvents include pyridine, dioxane, and dimethylformamide. The solvents may be used in their neat form, mixed together, or mixed with other co-solvents to improve the mixtures properties such as lowering or raising the volatility or viscosity. The solvent is then removed by, for example, by pouring the mixture onto a surface and letting the solvent evaporate.

The fluorescent properties of the microparticles are measured under set conditions and recorded. For example, the fluorescence intensity of 1 mg of beads in 500 ul of water can be measured and recorded. In this manner, large batches of uniformly-imbibed microparticles with desired physical properties, such as size and charge density, can be prepared.

In instances where it is desirable to imbibe the polymer with a mixture of dyes, the selected dyes for the mixture can be imbibed sequentially. Alternatively, the selected dyes can be imbibed into the polymer simultaneously. The ratio of dyes employed in the mixture will vary depending on the nature of the dyes and the desired combination of spectral properties.

5.15 Improved Properties

The fluorescent polymeric materials containing the lipid soluble rhodamine dyes, when excited by a light source, emit an unusually strong spectral signal with low background noise. The spectral signal is dependent upon the identities, concentration and ratio of the dyes in the polymer.

Furthermore, hydrophobic polymeric materials containing the lipid soluble rhodamine dyes exhibit enhanced dye retention in aqueous solvent. The dyes are not significantly removed from the polymers by the water-based solvents commonly used in biologic assays as a suspension medium. This is accomplished, in part, by the selection of lipophilic substituents, often attached to the amine and imminium moieties, that impart a lipophilic nature to the rhodamine dyes.

Finally, fluorescent polymeric materials containing the lipid soluble rhodamine dyes are highly photo and chemically stable. In fact, some of the lipid soluble rhodamines have photostabilities as high as ten times that of fluorescein and 100 times that of cyanine.

In summary, the fluorescent polymeric materials of the instant invention enjoy all of the benefits associated with the use of rhodamine dyes while avoiding the detriments that previously made rhodamine dyes undesirable for such applications.

5.16 Additional Substances

The fluorescent polymeric material may also optionally include one or more other substances absorbed, adsorbed or covalently attached thereto. As stated above, a non-limiting list of such substances includes biomolecules, drugs, poisons, vitamins, antigens and pathogens (including viruses, fungi and bacteria) as well as molecules that can act as a probe for a biomolecule, such as biotin. Non-limiting examples of biomolecules include amino acids, polypeptides, glycosolated and unglycosolated proteins, nucleosides, nucleotides, oligonucleotides, polynucletides, nucleic acids, polynucleic acids such as DNA and RNA, carbohydrates, and steroids. Compounds often classed by their functionality rather than structure are also included, e.g., haptens, toxins, antibodies, enzymes and hormones. In addition, the additional substance can be a probe for a biomolecule, such as biotin. Generally, these substances are either covalently attached to the polymer component of the fluorescent polymeric material, e.g., through the one or more of the "activations" discussed above or incorporated non-covalently by absorption into, or adsorbtion onto, the polymer component. In one embodiment, one or more of these substances are covalently attached to the polymer.

5.17 Illustrative Uses

The fluorescent polymeric materials of the invention can be used for passive or covalent coupling of biological material, i.e., analyte or analytical reactant, such as haptens, antigens, antibodies, enzymes or nucleic acids and used for various types of analyte assays such as immunoassays, nucleic acid (DNA or RNA) assays, affinity purification, cell separation and other medical diagnostic, and industrial applications.

In one aspect of the invention, a mixture of lipid soluble rhodamine dyes and, optionally, additional dyes, are internally incorporated, simultaneously or sequentially, into a polymeric microparticle population to give the microparticle population a unique spectral signature or "bar code." In determining the proportion of each of the dyes to be used to generate the bar code, the intensity values for the spectral profiles of each of the dyes (at standard concentrations) are determined in solution at an excitation wavelength desired to be used. The intensity values for each spectral profile are added together to get a composite spectral emission profile, and the relative proportions of each of the dyes are adjusted to give a composite spectral emission. The addition of spectral profiles and the adjustment of relative proportions is readily simulated on a computer (starting with the standard experimental values determined in the previous step), and these proportions are optionally adjusted in practice.

A number of particle populations are created, each characterized by a different spectral bar code. The particles can then be activated or otherwise modified so that they have a specific reactivity with one or more substances to be measured or assayed (analytes) in a clinical or test sample. Thus, the spectral bar code in each particle population corresponds to a different known reactivity. The particle populations can then be blended in a specified ratio to form a multicolored particle mixture. Imbibed bead mixtures may contain hundreds to thousands of fluorescent dye molecules which greatly increases the sensitivity of assays employing bead labels in comparison to single dye assays.

To achieve truly multiplexed analysis of a plurality of analytes in a single sample, some form of identifiable marker, for instance a third type of fluorescent dye or a probe for a biomolecule (e.g., biotin) should be provided that is capable of binding the analyte of interest. This marker has two functions, namely, the capacity to react with the analyte and the capacity to be detected.

In one embodiment, the microparticles containing bound particles are then separated and analyzed by conventional methods. Alternatively, all of the microparticles can be analyzed at the same time. Once again, the marker, e.g., a fluorescent dye or biotin, identifies the presence of an analyte on a given microparticle. The microparticle's fluorescent bar code identifies its specific reactivity. In this manner, the invention assists in the detection, differentiation, separation, quantification and analysis of analytes in a single mixture.

The particle populations may be analyzed by any fluorescence detection system, including visual inspection. However, automated techniques are preferred. Fluorescently imbibed microparticles are particularly well suited for flow cytometry analysis. An ordinary flow cytometer is capable of analyzing spectral properties (fluorescent signals) of up to 20,000 particles per second and can provide reliable quantitative data on a real-time scale.

Spectral differences that may be observed include, but are not limited to, a difference in excitation maxima, a difference in emission maxima, a difference in fluorescence lifetimes, a difference in fluorescence emission intensity at the same excitation wavelength or a different wavelength, a difference in absorption, a difference in fluorescence polarization, a difference in fluorescence enhancement in combination with target materials, or combinations thereof.

The analyte and analyte reactant pairs that may be employed vary widely. For example, the analyte and analyte reactant may be selected from any of the following combinations wherein either member of the combination may be the analyte or the binding partner: antigen and specific antibody; hormone and hormone receptor; hapten and anti-hapten; polynucleotide and complementary polynucleotide; polynucleotide and polynucleotide binding protein; biotin and avidin or streptavidin; enzyme and enzyme cofactor; and lectin and specific carbohydrate.

The haptens include naturally occurring hormones, naturally occurring drugs, synthetic drugs, pollutants, allergens, affector molecules, growth factors, chemokines, cytokines, lymphokines, amino acids, oligopeptides, chemical intermediates, nucleotides, oligonucleotides or the like. The use for such compounds may be in the detection of drugs of abuse, therapeutic dosage monitoring, health status, donor matching for transplantation purposes, pregnancy (e.g., hCG or alpha-fetoprotein), detection of disease, e.g., endotoxins, cancer antigens, pathogens, and the like. Therapeutic drugs may include, but are not limited to, anti-AIDS substances, anti-cancer substances, antibiotics, anti-viral substances, enzyme inhibitors, neurotoxins, opioids, hypnotics, antihistamines, tranquilizers, anti-convulsants, muscle relaxants and anti-Parkinson substances, anti-spasmotics and muscle contractants, miotics and anti-cholinergics, immunosuppressants (e.g., cyclosporine) anti-glaucoma solutes, anti-parasite and/or anti-protozoal solutes, anti-hypertensives, analgesics, anti-pyretics and anti-inflammatory agents (such as NSAID's), local anesthetics, ophthalmics, prostaglandins, anti-depressants, anti-psychotic substances, anti-emetics, imaging agents, specific targeting agents, neurotransmitters, proteins and cell response modifiers. Proteins are of interest in a wide variety of diagnostics, such as detecting cell populations, blood type, pathogens, immune responses to pathogens, immune complexes, saccharides, lectins, naturally occurring receptors, and the like. Receptors may find use in binding to haptens, proteins, other receptors, or the like, or detection of the presence of pathogens, the level of a particular protein in a physiological fluid, the presence of haptens in a wide variety of samples, such as physiological fluids, air, process streams, water, etc. Nucleic acids may also find use in the detection of complementary strands, proteins specifically binding to nucleic acids and the like.

The analyte reactant can be also be selected among fluorescent reporter molecules capable of reacting with a variety of inorganic analytes that define properties of biological fluids, air, and the like, e.g., $O_2$, $CO_2$, $Ca^{++}$, $Na^+$, $K^+$, or $Cl^-$.

Of particular interest is the binding of microorganisms and cells, including viruses, prokaryotic and eukaryotic cells, unicellular and polycellular organism cells, e.g., fungi, animal, mammal, etc., or fragments thereof. Usually, these large aggregations will be non-covalently bound to the surface through specific binding pair member complexes. By having a high density of binding members bound to the surface, a cell or virus may be complexed by a large number of binding pair members, providing very strong anchoring of the cell, virus, or fragment. The system may then be subjected to vigorous treatment without concern for dislodging the specifically bound entity, while non-specifically bound materials may be readily removed.

The fluorescent polymeric materials of the invention may also be used for detecting pathogens. Monoclonal antibodies may be linked to the surface to serve as antibodies. The sample would then be added and cells having the epitope recognized by the antibody would bind to the antibody on the surface. Non-specifically bound pathogens are washed away leaving substantially only specifically bound ones. Labeled monoclonal antibodies are then added which are specific for an epitope other than the epitope recognized by the catching antibody. The term epitope is synonymous to term antigenic determinant and as used herein means a defined domain on the molecule that serves as a reaction or binding site. A molecule may have more than one epitope. For example, first epitope would allow coupling of the analyte with respective analytical reactant and second epitope will provide a binding site or domain for the labeling reagent. In contrast, a competitor molecule will be interfering (competing) with the formation of a binding pair analyte-analytical reactant. After incubating to allow reaction between the antibodies and pathogens, non-specifically bound antibodies are washed away and the presence of the label determined according to standard detection methods. Non-limiting examples of pathogens of interest include Herpesviruses, Poxviruses, Togaviruses, Orthomyxoviruses, Paramyxoviruses, Rhabdoviruses, Coronaviruses, Arenaviruses, and Retroviruses. They may also include bacteria including but not limited to *Escherichia coli, Pseudomonas aeruginosa, Enterobacter cloacae, Staphylococcus aureus, Enterococcus faecalis, Klebsiella pneumoniae, Salmonella typhimurium, Staphylococcus epidermidis, Serratia marcescens, Mycobacterium bovis*, methicillin resistant *Staphylococcus aureus* and *Proteus vulgaris*.

Assays using particles of the invention can be carried out in a biological fluid, including separated or unfiltered biological fluids such as urine, cerebrospinal fluid, pleural fluid, synovial fluid, peritoneal fluid, amniotic fluid, gastric fluid, blood, serum, plasma, lymph fluid, interstitial fluid, tissue homogenate, cell extracts, saliva, sputum, stool, physiological secretions, tears, mucus, sweat, milk, semen, vaginal secretions, fluid from ulcers and other surface eruptions, blisters, and abscesses, and extracts of tissues including biopsies of normal, malignant, and suspect tissues or any other constituents of the body which may contain the analyte of interest. Other similar specimens such as cell or tissue culture or culture broth are also of interest. Alternatively, the sample is obtained from an environmental source such as soil, water, or air; or from an industrial source such as taken from a waste stream, a water source, a supply line, or a production lot. Industrial sources also include fermentation media, such as from a biological reactor or food fermentation process such as brewing; or foodstuff, such as meat, game, produce, or dairy products. The test sample can be pre-treated prior to use, such as preparing plasma from blood, diluting viscous fluids, or the like; methods of treatment can involve filtration, distillation, concentration, inactivation of interfering compounds, and the addition of reagents.

5.18 Inherent Limitations In Structures

Those skilled in the art will appreciate that many of the lipid soluble rhodamine dye compounds described in the various structures herein may exhibit the phenomena of tautomerism, conformational isomerism, geometric isomerism and/or stereo isomerism. As the structures presented in the specification and claims can represent only one tautomeric, conformational isomeric, enantiomeric or geometric isomeric form, it should be understood that the invention encompasses any tautomeric, conformational isomeric, enantiomeric and/or geometric isomeric forms of the compounds that have one or more of the utilities described herein. As a specific example, reference is made throughout the specification to the C3 amino and C6 imminium substituents. As this nomenclature corresponds to the illustrated structures, which represent only one of several possible tautomeric forms (or resonance structures) of the compounds, it will be understood that these references are for convenience only and that any such references are not intended to limit the scope of the compounds described herein.

Furthermore, those of skill in the art will recognize that the lipid soluble rhodamine dyes of the invention may exist in many different protonation states, depending on, among other things, the pH of their environment. The structures provided herein depict the compounds in only one of several possible protonation states. Accordingly, it will be understood that these structures are illustrative only, and that the invention is not limited to any particular protonation state—any and all protonated forms of the dyes are intended to fall within the scope of the invention.

As the lipid soluble rhodamine dye compounds used in the invention may bear positive charges, depending upon their physical state, they often have counterions associated therewith. The identity or identities of any associated counterions is typically dictated by the synthesis and/or isolation methods by which the compounds are obtained. Typical counterions include, but are not limited to, halides, acetate, trifluoroacetate, any salt of a strong acid, and mixtures thereof. It will be understood that the identity or identities of any associated counterions is not a critical feature of the invention and that the invention encompasses the use of dyes in association with any type of counter ion. Moreover, as the compounds can exists in a variety of different forms, the invention is intended to encompass not only forms of the dyes that are in association with counterions (e.g., dry salts), but also forms that are not in association with counterions (e.g., aqueous or organic solutions).

5.19 Incorporation By Reference

All publications, patents and patent applications mentioned in this specification are herein incorporated by reference to the same extent as if each individual publication, patent or patent application was specifically and individually indicated to be incorporated by reference. No admission is made that any reference cited in this specification is prior art.

6. EXAMPLES 6.1 Experimental Overview

Figure 1:
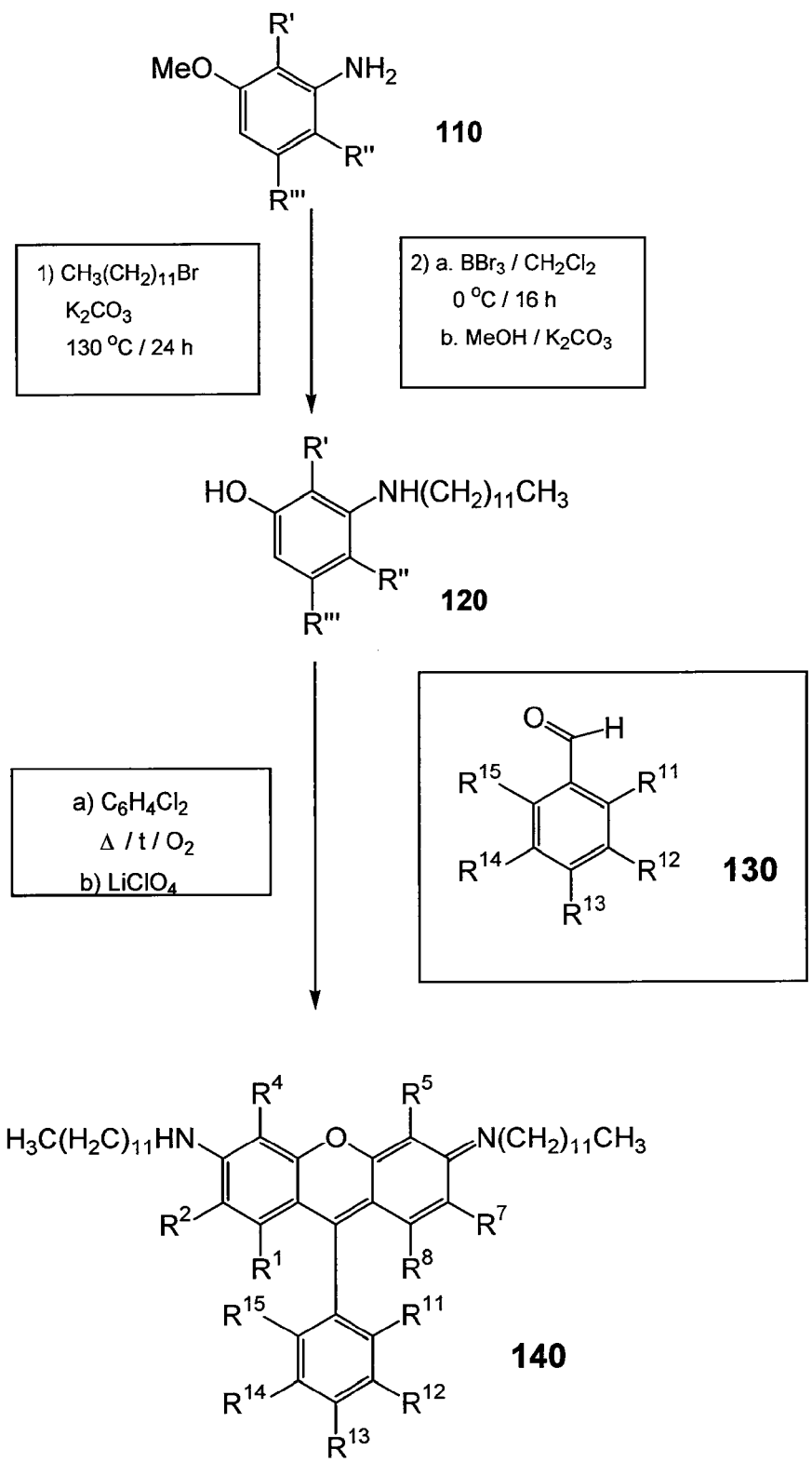
FIG. 1 is a first illustrative synthesis for the formation of one type of lipid soluble rhodamine dye.
Figure 2:
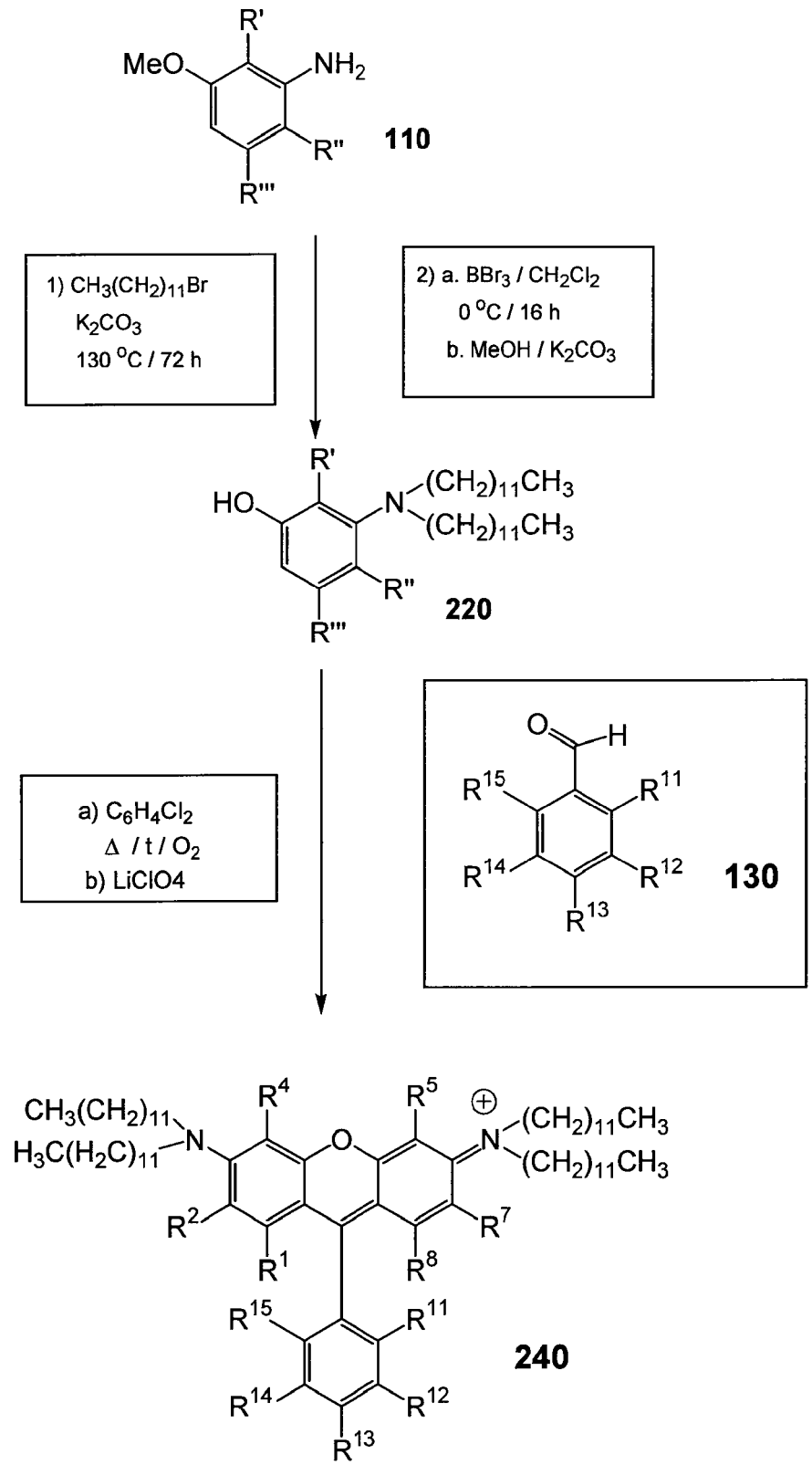
FIG. 2 is a second illustrative synthesis for the formation of a second type of lipid soluble rhodamine dye.
Figure 3:
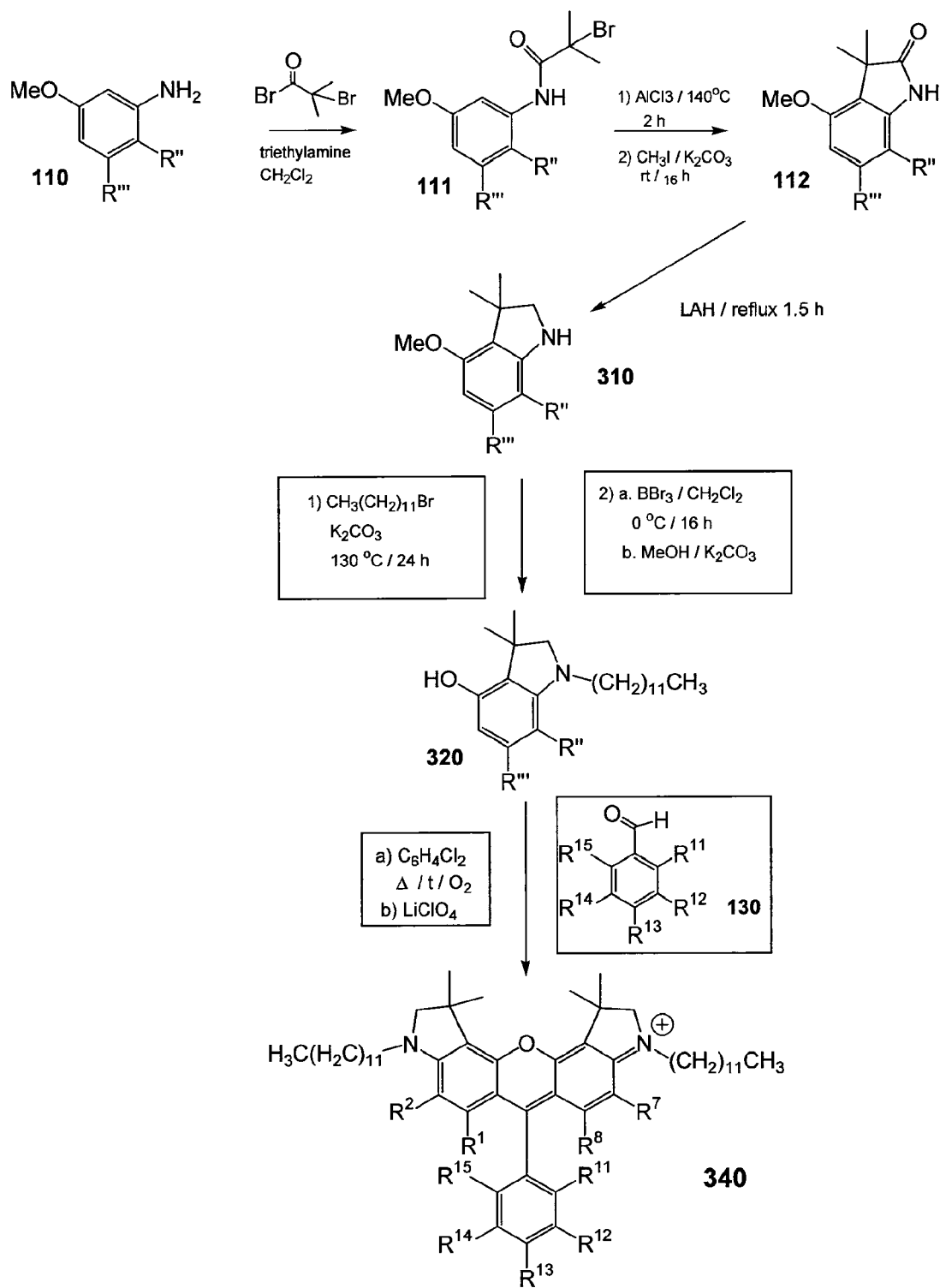
FIG. 3 is a third illustrative synthesis for the formation of a third type of lipid soluble rhodamine dye.

Lipid soluble rhodamine dyes were synthesized from reactions of substituted and un-substituted 1-hydroxy-3 aminobenzene derivatives with phenyl aldehyde derivatives (Examples 1, 2, and 3; FIGS. 1, 2, and 3). In general, the N-alkyl-1-hydroxy-3-amino-benzene intermediates were generated from N-alkyl-1-amino-3-methyoxybenzene derivatives. The N-alkyl 1-amino-3-methyoxybenzene derivatives were synthesized by N-alkylation of 1-amino-3-methyoxybenzene derivatives. In general, phenyl aldehyde derivatives and amino-3-methyoxybenzene derivatives were available from commercial sources (Aldrich Chemical company). Alternatively, lipid soluble rhodamine dyes were synthesized by a secondary derivatization of dyes first synthesized by established dye forming procedures (Example 4 and Example 5).

Following this general procedure, in accordance with the more detailed example descriptions below, the following dyes were obtained:

Dye (1)
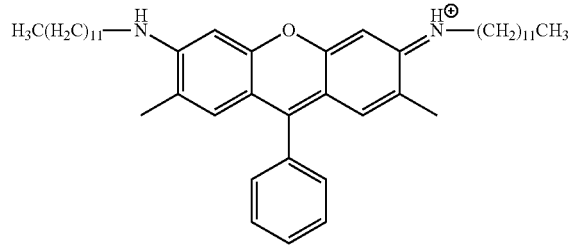

Dye (2)
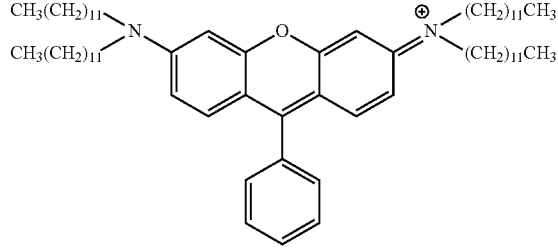

Dye (3)
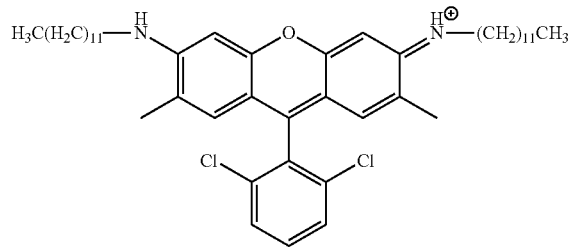

Dye (5)
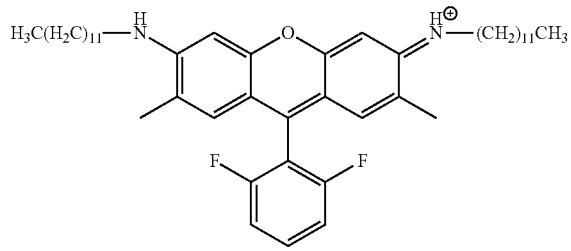

Dye (6)
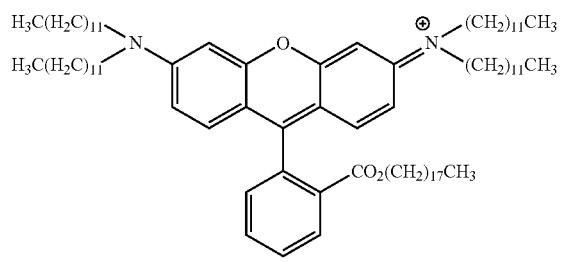

Dye (7)
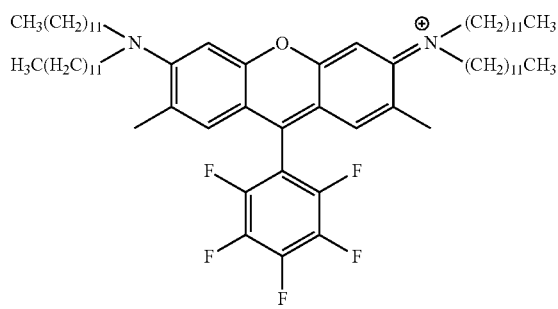

Dye (9)
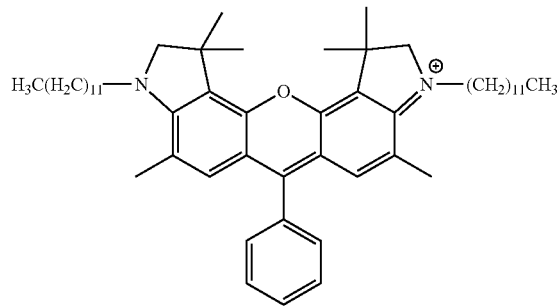

Dye (10)
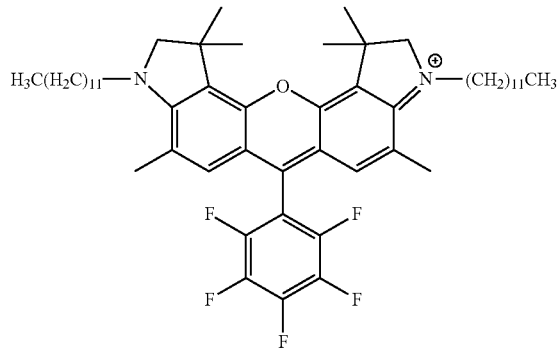

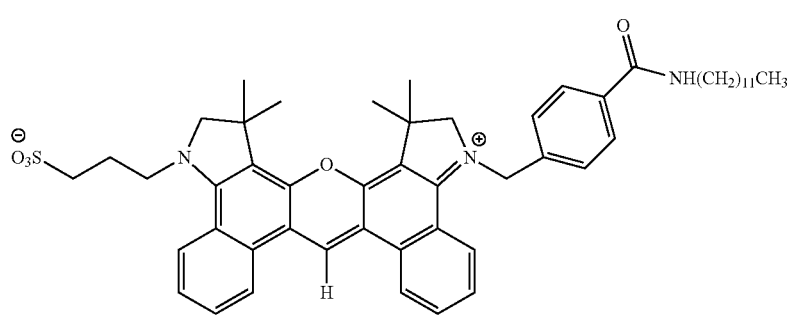

Dye (15)

Dye structures were verified by mass spectrometry (see Table 1 below).

6.2 Dye Synthesis

The general synthetic procedure for synthesis of bis N,N-dialkyl lipophilic rhodamine dyes of structure 140 is outlined in FIG. 1. 4-methyl-3-amino-1-methoxybenzene 110 (R'=R'''=H, R''=Me) was suspended in a neat solution of n-dodecylbromide in the presence of excess (10 equivalents) anhydrous $KHCO_3$ powder. The reaction was heated at 130° C. for 24 hours. The cooled reaction mixture was filtered through a plug of silica gel eluting with hexane and then ethyl acetate/hexane (1:20) to yield pure 4 methyl-3-dodecylamino-1-methoxy benzene 120 (R=Me, R'=R'''=H, R''=Me) in 70% yield ($^1$HNMR ($CDCl_3$) δ 7.02 (d, 1H), 6.27 (d, 1H), 3.86 (s, 3H), 3.54 (bs, NH), 3.20 (t, 2H), 2.14 (s, 3H), 1.74 (p, 2H), 1.41 (m, 18H), 0.98 (t, 3H))

As a general methyl group de-protection procedure, 4 methyl-3-dodecylamino-1-methoxy benzene 120 was suspended in dry $CH_2Cl_2$, cooled to 0° C. and 5 equivalents of a solution of $BBr_3$ (1M $CH_2Cl_2$, Aldrich Chem. Co.) were added and the reaction maintained at 0° C. for 16 hours. The reaction was quenched at 0° C. by slow addition of MeOH and then careful addition of solid $NaHCO_3$ (10 Equiv.) until foaming stops. The mixture was filtered, the filtrate was concentrated to an oil, and the product was isolated by normal phase chromatography eluting with methanol/$CH_2Cl_2$. The solvent was removed from the pure fractions to give 3-dodecylamino-1-hydroxy-4 methylbenzene 120 (R=H, R'=R'''=H, R''=Me) as a waxy solid in 70-80% yield ($^1$HNMR ($CDCl_3$) δ 6.91 (d, 1H), 6.17 (d, 1H), 6.14 (dd, 1H) 4.62 (bs, OH), 3.53 (bs, NH), 3.14 (t, 2 H), 2.09 (s, 3 H), 1.70 (p, 2 H), 1.46 (m, 18H), 0.93 (t, 3H))

As a general dye synthesis procedure, 3-dodecylamino-1-hydroxy-4 methylbenzene 120 (R=H) and a phenyl aldehyde of general structure 130 were suspended in dichlorobenezene and the reaction mixture was heated with stifling at 155° C. for 1 hour. Different phenyl aldehydes were found to require different temperatures and reaction times to produce optimal yields in the dye forming reaction. For example; when $R^{11}=R^{15}$=chlorine, a 30 minute reaction time at 145° C. resulted in complete conversion of starting materials, and when $R^{11}$-$R^{15}$=Fluorine a reaction time of 20 minutes at 135° C. was sufficient for complete conversion. The reaction mixture was allowed to cool and solid $LiClO_4$ was added with stirring. The resulting mixture was suspended in $CH_2Cl_2$ and loaded directly unto a small pack of silica gel. The silica pack was first eluted with $CH_2Cl_2$ and then with methanol/dichloromethane (1:99). The fractions containing dye were collected and concentrated to an oil.

Thus dyes 1, 3, and 5 of general structure I (where $R^4=R^5=R^1=R^8$=H, and $R^2=R^7$=Me) were produced by the general procedure in reactions of 120 (R=H, R'=R'''=H, R''=Me) with compounds 130 where $R^{11}$ to $R^{15}$=H, for Dye 1, $R^{11}=R^{15}$=chlorine and $R^{12}$ to $R^{14}$=H for Dye 3, $R^{11}=R^{15}$=fluorine and $R^{12}$ to $R^{14}$=H for Dye 5.

6.3 Dye Synthesis

The general synthetic procedure for synthesis of N,N, N', N'-tetraalkyl lipophilic rhodamine dyes of structure 240 is outlined in FIG. 2. 3-amino-1-methoxybenzene 110 was suspended in a neat solution of n-dodecylbromide in the presence of excess (10 equivalents) anhydrous $KHCO_3$ powder. The reaction was heated at 130° C. for 72 hours. The cooled reaction mixture was filtered through a plug of silica gel eluting with hexane and then ethyl acetate/hexane (1:20) to yield pure 3-(N,N-didodecylamino-1-methoxy benzene 220 (R=Me, R'=R''=R'''=H) in 70% yield ($^1$HNMR ($CDCl_3$) δ 7.15 (t, 1 H), 6.31 (d, 1 H), 6.24 (m, 2 H), 3.83 (s, 3 H), 3.27 (t, 4 H), 1.60 (p, 4 H), 1.34 (m, 36 H), 0.93 (t, 6 H))

By the general de-protection procedure described for 120, methyl group de-protection of 220 (R=Me) gave 3-(N,N-didodecylamino-1-hydroxy-4 methylbenzene 220 (R=H, R'=R''=R'''=H) as a waxy solid in 70-80% yield ($^1$HNMR ($CDCl_3$) δ7.08 (t, 1 H), 6.27 (dd, 1 H), 6.16 (t, 1 H), 6.13 (dd, 1H), 4.61 (bs, OH), 3.25 (t, 4 H), 1.61 (p, 4 H), 1.33 (m, 36 H), 0.93 (t, 6 H)).

By the general dye synthesis procedure described for 140, 3-(N,N-didodecylamino-1-hydroxy-4 methylbenzene 220 reacted with phenyl aldehydes 130 to give dyes of general structure 240. As in synthesis of dye 140, different phenyl aldehydes required different temperatures and reaction times to produce optimal yields in the dye forming reactions.

Thus, dyes 2 and 7 of general structure I (where $R^1=R^2=R^4=R^5=R^7=R^8$=H) were produced by the reactions from starting materials 220 (R=H, R'=R''=R'''=H) and 130 where $R^{11}$ to $R^{15}$=H for Dye 2, $R^{11}=R^{15}$=chlorine and $R^{11}$ to $R^{15}$=fluorine for Dye 7.

6.4 Dye Synthesis

The general synthetic procedure for synthesis of N-alkyl indoline lipophilic rhodamine dyes of structure 340 is outlined in FIG. 3. 3-Amino-1-methoxybenzene 110 (R''=Me, R'''=H) was mixed with isobutyryl bromide in $CH_2Cl_2$ and 3 equivalents of triethylamine were added drop-wise at 0° C. The reaction mixture was stirred for 2 hours, quenched by addition of dilute $H_2SO_4$, and the organic layer was separated and dried with $MgSO_4$. Purification by normal phase chromatography eluting with hexane:$CH_2Cl_2$ (1:1) gave 111 in 96% yield. The intermediate 111 was mixed with 5 equivalents $AlCl_3$ and heated at 140° C. for 2 hours. The mixture was cooled and the solid triturated with $CH_2Cl_2$. The solution was concentrated to an oil and then suspended in acetone. To the solution was added 10 equivalents methyl iodide and 15 equivalents $K_2CO_3$. The reaction was stirred overnight, filtered, and concentrated to an oil. Purification by normal phase chromatography eluting with hexane: $CH_2Cl_2$ (0.3:1) gave 112 in 60% yield. Intermediate 112 was suspended in tetrahydrofuran and the solution was added to a suspension of 5 equivalents of lithium aluminum hydride in tetrahydrofuran. The mixture was refluxed for 1.5 hours and then allowed to cool. The reaction was quenched at by slow addition of ice chips and then cold 1 M NaOH. The mixture was transferred to a separatory funnel and partitioned into ethyl acetate. The organic layer was dried with $Na_2SO_4$ and concentrated to an oil. The crude mixture was separated by normal phase chromatography eluting with hexane/ethyl acetate (1:10) to give 310 in 21% yield Following the general procedures outlined for synthesis of 120 from 110, N-alkylation of 310 with n-dodecylbromide and methyl group deprotection produced 320 (320 R═H, R"═Me, R'"═H; $H^1$NMR $CDCl_3$ 6.72 (d, 1 H), 6.08 (d, 1 H), 4.65 bs, OH), 3.27 (t, 2 H), 3.22 (s, 2 H), 2.29 (s, 3 H), 1.59 (p, 2 H), 1.45 (s, 6 H), 1.35 (m, 18 H), 0.94 (t, 3 H))

Following the general dye synthesis procedure described for 140, Lipophilic rhodamine dyes of structure 340 were synthesized. Thus, N-dodecyl-hydroxy-methylindoline 320 was reacted with phenyl aldehydes 130 and the fractions containing 340 were collected and concentrated to oils. By analogy to synthesis of dye 140, different phenyl aldehydes required different temperatures and reaction times to produce optimal yields in the dye forming reactions. Thus, Dyes 9 and Dye 10 of general structure I (where $R^7$═$R^2$═Me, $R^1$═$R^8$═H) were produced from starting materials 320 ((R═H, R"═Me, R'"═H) and 130 where $R^{11}$ to $R^{15}$═H for Dye 9, and $R^{11}$ to $R^{15}$═fluorine for Dye 10.

6.5 Dye Synthesis

Lipophilic rhodamine dyes of the general structure 140 and 240, where one or more of $R^{11}$ to $R^{15}$ equal carboxylate ester, were synthesized from the carboxylate dye intermediates which had been first synthesized by established procedures. In general, carboxylate substituted dyes were produced by reaction of trimellitic acid anhydride derivatives or phthallic anhydride derivatives with aminohydroxybenzene derivatives, such as 120, 220, or 320 in methanesulfonic acid with heating.

The carboxylate acid groups were esterified by reaction of the dye acid with the alcohol under standard acid catalyzed esterification conditions. Thus, Dye 6 was generated by reaction of 220 (R═H, R"═Me, R'═R'"═H) with phthallic anhydride followed by esterification with octadecyl alcohol (Dye 6; 240 where $R^{11}$═octadecyl carboxy ester, $R^{12}$ to $R^{15}$═H, $R^1$═$R^2$═$R^7$═$R^8$═H).

6.6 Dye Synthesis

Lipophilic rhodamine dyes of general structure (II) (where $R^9$═H) were synthesized by secondary derivatization of carboxylate substituted dyes first synthesized according established procedures as illustrated, for example, in U.S. Pat. No. 5,936,087 (Benson et al.). In general, dyes of general structure (II) were produced by reaction of DMF and $POCL_3$ with aminohydroxybenzene derivatives of general structure 310 (where R=Me, R" to R" bridged benzo). N-Aryl or N-alkyl carboxylate derivatives of 310 were synthesized by established procedures. Amidation of carboxy substituted dyes of general structure (II) was typically performed by NHS ester activation and reaction with the preferred amine. Thus, Dye 15 was generated by reaction of the Dye NHS with dodecylamine.

6.7 Spectral Analysis

Concentrated stocks of the dye were made by suspending the dye in ethyl acetate or $CH_2Cl_2$. Absorption spectra of equal aliquots of the dyes were recorded (HP model 8451A diode array spectrophotometer) in methanol and toluene, and the spectra were monitored for changes in absorption intensity and wavelength. In general, dyes with good spectral properties in non-polar organic solvents, such as toluene, were considered good candidates for polystyrene imbibing. An extinction coefficient equal to 80,000 for the dyes in methanol was used to approximately determine the dye concentrations for fluorescence measurements and bead imbibing experiments. Fluorescence emission and excitation spectra were recorded for diluted dye stocks in methanol and toluene at equal concentrations of the dyes ($0.6\times10^{-6}$ M).

TABLE 1

Spectral Analysis

| Dye | Mass Spectrum Calc./Observed | Emission λmax MeOH (nm) | Emission λmax Toluene (nm) | Emission λmax Beads (nm) |
|---|---|---|---|---|
| 1 | 650.52/$[M + H]^+$ 651.6 | 553 | 560 | 548 |
| 2 | 959.9/$[M]^+$ 960.0 | 586 | 586 | 586 |
| 3 | 718.44/$[M + H]^+$ 719.52 | 564 | 575 | 579 |
| 5 | 686.5/$[M + H]^+$ 687.6 | 562 | 579 | 573 |
| 6 | 1256.1/$[M]^+$ 1256.21 | 588 | 596 | 587 |
| 7 | 1049.8/$[M]^+$ 1050.0 | 613 | 612 | 612 |
| 9 | 759.62/$[M]^+$ 759.63 | 615 | 626 | 616 |
| 10 | 849.57/$[M]^+$ decomp | 661 | 657 | 659 |
| 15 | 841.46/$[M + H]^+$ 842.60 | 652 | 655 | 654 |

6.8 Bead Coding Assays

A general procedure was followed to imbibe polystyrene beads with the lipophilic rhodamine dyes 1, 2 and 9, both individually and in combination. The polystyrene beads were typically 1-10 um in diameter, preferably 5 um in diameter, and contained from 1 to 20%, preferably from 1 to 5%, crosslinking. Such beads are commercially available from a number of sources (e.g., Bangs labs, Dynal, Spereotech, Polyscience). The dye stocks were set at $1\times10^{-3}$ molar in ethyl acetate. Three milligrams of dry beads were weighed into a eppendorf tube. Different amounts of dye stocks were diluted into ethyl acetate, either as a mixture or as a single dye. The diluted ethyl acetate solutions were added at once to the beads. The beads were kept in contact with the dye solutions for 1 hour and then 5 fold volume of isopropanol was added to the bead suspension. The beads were kept at room temperature for an additional 30 minutes and then the tube was centrifuged down and the dye solution separated from the beads. The beads were washed with isopropanol. The fluorescence intensity of the beads was recorded for a ⅓ dilution of the beads in water suspended in 500 ul of water (1 mg/500 ul). FIG. 4 shows the emission spectrum of beads imbibed with a mixture of the three dyes in comparison to beads imbibed with each dye alone and the predicted sum of the three single dye spectra.

6.9 Fluorescent Reference Standards

Three grams of polystyrene plastic are dissolved in 10 ml of a suitable neutral organic solvent with agitation. Preferred solvents include chlorinated aliphatic solvents such as dichloromethane, chloroform, and carbon tetrachloride. Alternative solvents include aromatic hydrocarbons such as benzene, toluene, and xylene. Other solvents include pyridine, dioxane, and dimethylformamide. The solvents may be used in their neat form, mixed together, or mixed with other co-solvents to improve the mixtures properties such as lowering or raising the volatility or viscosity. A lipophilic rhodamine dye is suspended in the dichloromethane or another preferred solvent to give a concentrated stock solution. Usually the dye is suspended in the same solvent as that used to dissolve the polystyrene. The stock concentration is determined spectrophotometrically. An aliquot of the concentrated stock is mixed into a portion of the pre-mixed polystyrene solution to give the desired dye concentrations of from 1×10-3 to 1×10-15 M, preferably 1×10-6 M to 1×10-9 M. The dye polystyrene mixture is pipetted or poured into a mold or spotted onto a surface and let sit from 5 to 24 hours until the solvent evaporates. If desired, the resultant solid dyed polystyrene can also be machined. The solid dyed polystyrene is then used as a fluorescent reference standard for testing fluorescence intensity or spectral shape in quality control analysis of fluorescence detection based instruments. Similarly, the dyed polystyrene can be formed in wells of microtiter plates and fluorescence measurements used to establish well location or set focal depths of fluorescence based instruments.

What is claimed:

1. A fluorescent polymeric material comprising a polymeric particle and at least one lipid-soluble rhodamine dye comprising the following core structure:

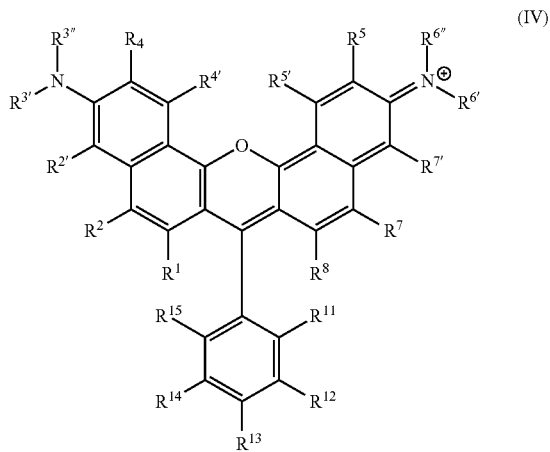

(IV)

wherein $R^1$ and $R^8$ are each, independently of one another, selected from the group consisting of hydrogen, (C1-C20) alkyl and halo, or one of $R^1$ or $R^8$ is part of an optionally substituted benzo group with $R^2$ or $R^7$, respectively, and the other one of $R^1$ and $R^8$ is selected from hydrogen, (C1-C20) alkyl and halo;

$R^2$ is selected from the group consisting of hydrogen, (C1-C20) alkyl and halo, or alternatively, $R^2$ is taken together with $R^1$ or $R^{2'}$ to form part of an optionally substituted benzo group;

$R^{2'}$ is selected from the group consisting of hydrogen, (C1-C20) alkyl and halo, or alternatively, $R^{2'}$ is taken together with $R^2$ to form part of an optionally substituted benzo group, or alternatively, $R^{2'}$ is taken together with $R^{3'}$ to form an optionally substituted 5- or 6-membered ring;

$R^{3'}$ is selected from the group consisting of hydrogen, and (C4-C20) alkyl, or alternatively $R^{3'}$ is taken together with $R^{2'}$ to form an optionally substituted 5- or 6-membered ring;

$R^{3''}$ is selected from the group consisting of (C4-C20) alkyl, or alternatively $R^{3''}$ is taken together with $R^4$ to form an optionally substituted 5-membered ring;

$R^4$ is selected from the group consisting of hydrogen, C1-C20) alkyl and halo, or alternatively $R^4$ is taken together with $R^{3''}$ to form an optionally substituted 5-membered ring;

$R^{4'}$ is selected from the group consisting of hydrogen, (C1-C20) alkyl and halo;

$R^{5'}$ is selected from the group consisting of hydrogen, C1-C20) alkyl and halo;

$R^5$ is selected from the group consisting of hydrogen, C1-C20) alkyl and halo, or alternatively $R^5$ is taken together with $R^{6''}$ to form an optionally substituted 5-membered ring;

$R^{6'}$ is selected from the group consisting of (C4-C20) alkyl, or alternatively $R^{6'}$ is taken together with $R^{7'}$ to form an optionally substituted 5-membered ring;

$R^{6''}$ is selected from the group consisting of hydrogen, and (C4-C20) alkyl, or alternatively $R^{6''}$ is taken together with $R^5$ to form an optionally substituted 5-membered ring;

$R^{7'}$ is selected from the group consisting of hydrogen, (C1-C20) alkyl and halo, or alternatively, $R^{7'}$ is taken together with $R^{6'}$ to form an optionally substituted 5-membered ring, or alternatively, $R^{7'}$ is taken together with $R^7$ to form part of an optionally substituted benzo group;

$R^7$ is selected from the group consisting of hydrogen, (C1-C20) alkyl and halo, or alternatively, $R^7$ is taken together with $R^{7'}$ or $R^8$ to form part of an optionally substituted benzo group;

$R^{11}$ and $R^{15}$ are each hydrogen or are each F or Cl;

$R^{12}$, $R^{13}$ and $R^{14}$ are each hydrogen or are each F or Cl;

wherein at least one of $R^{3'}$, $R^{3''}$, $R^{6'}$ and $R^{6''}$ is a (C4-C20) alkyl; and wherein the lipid-soluble rhodamine dye is incorporated into the polymeric particle non-covalently.

2. The fluorescent polymeric material of claim 1, wherein the polymeric particle is composed of a particle formed by polymerizing one or more of the following monomers: substituted or unsubstituted styrenes, acrylate, alkyl acrylates, methacrylates, alkyl methacrylates, acrylonitrile, alkyl acrylonitrile, esters, acetates, amides, alcohols, acrolein, dimethylsiloxane, butadiene, isoprene, urethane, vinylacetate, vinylchloride, vinylpyridine, vinylbenzylchloride, vinyltoluene, vinylidene chloride and divinylbenzene, and mixtures thereof, with or without a crosslinking agent.

3. The fluorescent polymeric material of claim 1, wherein the polymeric particle is composed of a hydrophobic copolymer of styrene, acrylic acid and a polyvinyl crosslinking agent.

4. The fluorescent polymeric material of claim 1, wherein the polymeric particle is in the form of a microparticle having a diameter in the range of about 0.01 to 1000 micrometers.

5. The fluorescent polymeric material of claim 1 wherein the polymeric particle is activated with one or more groups that comprise a reactive functionality.

6. The fluorescent polymeric material of claim 5, wherein the reactive functionality is an electrophile selected from the group consisting of pentafluorphenyl ester, NHS-ester, acrylamides, acyl azides, acyl halides, aldehydes or ketones, alkyl halides, alkyl sulfonates, anhydrides, aryl halides, aziridines, bonorates, carboxylic acids, carbodiimides, diazoalkenes, epoxides, haloacetamides, halotriazines, imido esters, isocyanates, isothiocyanates, maleimides, phosphoramidites, silyl halides, sulfonate esters and sulfonyl halides.

7. The fluorescent polymeric material of claim 5, wherein the reactive functionality is a nucleophile selected from the group consisting of amines/anilines, alcohols/phenols, thiols, hydrazines and hydroxylamines.

8. The fluorescent polymeric material of claim 1, further comprising another substance that is absorbed into, adsorbed onto or into, or covalently attached to, the polymeric particle.

9. The fluorescent polymeric material of claim 8, wherein the another substance is selected from the group consisting of a biomolecule and a probe for a biomolecule.

10. The fluorescent polymeric material of claim 1, further comprising from one to nine additional fluorescent dye types non-covalently incorporated into the polymeric particle.

11. The fluorescent polymeric material of claim 10, wherein each of the additional fluorescent dye types is, independently of the others, selected from the group consisting of: a lipid-soluble rhodamine dye according to structural formula (IV), an additional lipid-soluble rhodamine dye and lipid-soluble form of: an acridine dye, an alizarine dye, an azo dye, an anthraquinine dye, a BODIPY dye, a coumarin dye, a cyanine dye, a fluorescein dye, a lanthanide complex, an oxazine dye, a phenazathionium dye, a phenazoxonium dye, a porphyrin dye, a pyrene dye, a pyrilium dye, a perylene dye, a phenoxazine dye, a phenezine dye, a rhodol dye and a xanthene dye.

12. The fluorescent polymeric material of claim 10, wherein all of the fluorescent dyes fluoresce when irradiated with the same excitation source.

13. The fluorescent polymeric material of claim 10, wherein two or more of the fluorescent dyes fluoresce when irradiated with multiple excitation sources.

14. The fluorescent polymeric material of claim 10, wherein at least one of the fluorescent dyes is an energy transfer dye.

15. A collection of fluorescent polymeric particles, each of which has a unique, spectrally resolvable fluorescence emissions spectrum, wherein at least one of the polymeric particles is a polymeric material according to claim 1.

* * * * *